United States Patent [19]
Abu El-Haj et al.

[11] 3,962,264
[45] June 8, 1976

[54] PROCESS FOR MAKING 2-AMINO NICOTINONITRILE

[75] Inventors: Marwan J. Abu El-Haj, Gales Ferry; Beryl William Dominy, Groton, both of Conn.

[73] Assignee: Pfizer Inc., New York, N.Y.

[22] Filed: Sept. 23, 1974

[21] Appl. No.: 508,060

Related U.S. Application Data

[62] Division of Ser. No. 292,645, Sept. 27, 1972, Pat. No. 3,862,191.

[52] U.S. Cl. ............................................. 260/294.9
[51] Int. Cl.² ........................................ C07D 213/84
[58] Field of Search ................................. 260/294.9

[56] References Cited
OTHER PUBLICATIONS

Migrdichian "Chemistry of Organic Cyanogen Compounds" (1947) pp. 277 and 329.
Abramovitch "Pyridine and Its Derivatives" Supplement pt. 3 (1974) p. 624.

*Primary Examiner*—Natalie Trousof
*Assistant Examiner*—R. W. Ramsuer
*Attorney, Agent, or Firm*—Connolly and Hutz

[57] ABSTRACT

2-Substituted pyridopyrimidines and their alkali and alkylamine salts as herbicides, and processes for the synthesis of starting materials leading to the preparation thereof.

3 Claims, No Drawings

PROCESS FOR MAKING 2-AMINO NICOTINONITRILE

CROSS REFERENCE TO RELATED APPLICATION

This application is a division of application Ser. No. 292,645 filed Sept. 27, 1972 and now U.S. Pat. No. 3,862,191.

BACKGROUND OF THE INVENTION

This invention relates to 2-substituted pyrido[2,3-d]-, pyrido[3,4-d]- and pyrido[4,3-d]pyrimidin-4(3H)-one and their use as herbicidal agents, and to processes for the preparation of 2-aminonicotinonitriles, useful as intermediates in the synthesis of the subject compounds.

Weeds, which can be broadly defined as any undesirable plants, cause considerable economic losses annually and are also objectionable for aesthetic reasons. Considerable effort is expended annually for removing and controlling the growth of weeds along highways, railway beds and in parks and gardens. Of most concern, however, is their interference with the growth of agricultural crops, thereby increasing the cost of producing these crops. Weeds are generally eliminated mechnically, such as by actual physical removal from the ground or by means of chemicals. Initially, the chemicals used for weed control were inorganic compounds, in particular the chlorates, chlorides and arsenites. These compounds are usually non-selective herbicides and kill all living plants. In the 1940's, attention was directed to more selective herbicides which would only destroy undesirable plants and cause little damage to agricultural crops. Most of these new herbicides were organic compounds and the first one developed, 2,4-D (2,4-dichlorophenoxyacetic acid) and its derivatives, is still widely used today for weed control.

In the interest of economy and selectivity, many other prototype organic structures have been examined for herbicidal activity. A limited series of quinazolines including 4-ethylamino-, 4-diethylamino-, 2-chloro-4-ethylamino- and 2-chloro-4-diethylaminoquinazoline are claimed as plant-growth regulators, British Patent No. 822,069. In 1964–65, Deysson, et al., Compt. Rend., 259 (2), 479 (1964), Ann. Pharm. Franc., 23, 163, 229 (1965) reported the antimitotic properties of 1-methyl-1,4-dihydro-, 1-propyl-1,4-dihydro-, 3-methyl-3,4-dihydro-, 3-ethyl-3,4-dihydro-, 3-propyl-3,4-dihydro-, and 3-isopropyl-3,4-dihydro-4-quinazolones. U.S. Pat. No. 3,244,503 discloses a series of 3-alkyl and cycloalkyl substituted 2,4(1H,3H)-quinazolinediones, useful as herbicides.

The synthesis of 2-mercaptopyrido[2,3-d]pyrimidin-4(3H)-one derivatives, as diuretic and saluretic agents, is reported in British patent 1,272,060 and West German patent application 2,036,063, and the corresponding 2-hydroxypyrido[2,3-d]pyrimidin-4(3H)-ones in French patent 2,085,750, also claimed as diuretic agents.

Antiphlogistic and antipyretic activity is claimed for 2,3-disubstituted derivatives of pyrido[2,3-d]pyrimidin-4(3H)-ones in East German patent 49,610, while herbicidal and plant growth regulatory activity is claimed for 1,3-disubstituted pyrido]3,2-d]pyrimidin-2,4(1H,3H)-diones, West German patent application 1,932,160.

Ried, et al., Justus Liebigs Ann. Chem., 707, 250 (1967), have reported the preparation of 2-methyl-pyrido[3,4-d]pyrimidin-4(3H)-one and Dornow, et al., Chem. Ber., 98, 1505 (1965), the synthesis of a series of pyrido[2,3-d]pyrimidin-4(3H)-ones; neither study disclosed a utility for the prepared compounds.

SUMMARY OF THE INVENTION

It has now been discovered that novel pyridopyrimidin-4(3H)-ones of the formulae

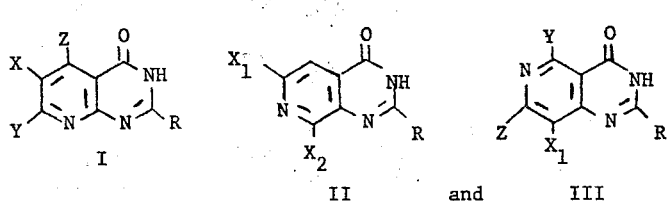

and the alkali metal and alkylamine salts thereof, wherein R is selected from the group consisting of alkyl containing from 3 to 5 carbon atoms, cycloalkyl containing 3 to 5 carbon atoms and —$CF_2R_1$ wherein $R_1$ is selected from the group consisting of F, Cl, H and —CLMN wherein L, M and N are each selected from the group consisting of H, F and Cl;

X is selected from the group consisting of H, Cl, Br and alkyl containing from 1 to 4 carbon atoms;

$X_1$ and $X_2$ are each selected from the group consisting of H, Cl and Br; and Y and Z are each selected from the group consisting of H and $CH_3$, have unexpected utility as herbicidal agents.

The preferred compounds of the present invention are those of formula I wherein X is Cl and Y and Z are H or $CH_3$.

A second class of preferred compounds are of formula I wherein X is alkyl of 3 to 4 carbon atoms and Y and Z are hydrogen.

Also considered within the scope of the present invention are compounds of the above formulae wherein R is alkyl or cycloalkyl each containing up to seven carbon atoms.

The present invention also embraces a process for the preparation of 2-aminonicotinonitrile, an intermediate useful in the synthesis of the final products, which comprises (1) reacting equimolar proportions of a 1,1,3,3-tetraalkoxypropane where said alkoxy contains from 1 to 4 carbon atoms with malononitrile in the presence of at least three molar equivalents of an alkanoic acid anhydride wherein said acid contains from 2 to 4 carbon atoms at 30°–200°C., and (2) thereafter contacting the intermediate 1-alkoxy-4,4-dicyano-1,3-butadiene with equimolar proportions of ammonia at 25°–100° C.

It is preferred that the initial condensation with the malononitrile be carried out at 50°–150° C. and in the presence of ZnCl$_2$, and that the condensation of the intermediate with ammonia be carried out at 25°–100° C.

Also within the scope of the present invention is a second process for the preparation of 2-amino-5-alkyl-nicotinonitriles of the formula

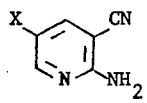

also comprises a method of inhibiting the growth of weeds by treating the soil before the emergence of the weed or the growing weeds themselves with a herbicidal amount of a compound selected from the groups given above.

DETAILED DESCRIPTION OF THE INVENTION

In accordance with the process employed for synthesizing the pyridopyrimidin-4(3H)-ones of the present invention, three preparative routes are amenable. The first is illustrted as follows:

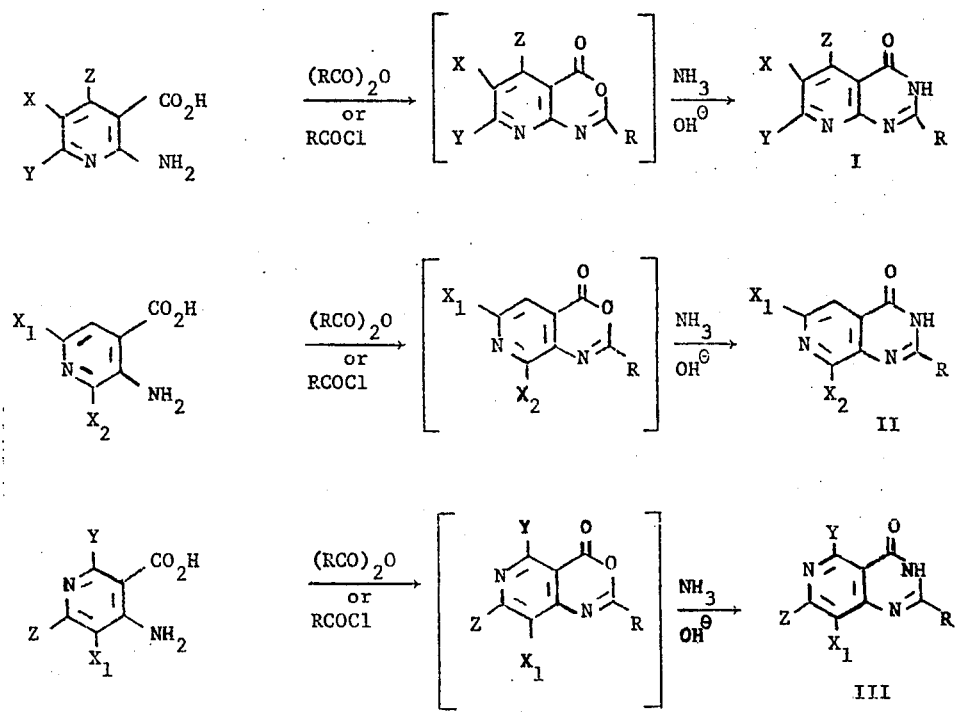

which comprises (1) contacting a compound of the formula

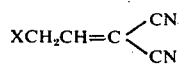

wherein X is alkyl containing from 1 to 4 carbon atoms, with equimolar proportions of a trialkyl orthoformte wherein said alkyl contains from 1 to 4 carbon atoms, in the presence of at least two molar equivalents of an alkanoic acid anhydride wherein said acid contains from 2 to 4 carbon atoms at 75°–175° C., and (2) thereafter, contacting the intermediate 1-alkoxy-2-alkyl-4,4-dicyano-1,3-butadiene with equimolar proportions of ammonia at 25°–150° C.

It is preferred that the initial condensation of the trialkyl orthoformate with the compound XCH$_2$CH=C(CN)$_2$ be carried out in the presence of a catalytic amount of a Lewis acid at 100°–150° C.

As previously mentioned, the aforesaid pyridopyrimidin-4(3H)-ones have been found to be effective in controlling the growth of weeds; the present invention In practice, the aminopyridine carboxylic acid, wherein X, Y, Z, X$_1$ and X$_2$ are as previously indicated, are contacted with an acid anhydride (RCO)$_2$O, or acid halide, preferably the acid chloride, RCOCl, in a suitable inert solvent.

Such a reaction-inert solvent comprising the liquid phase of said reaction should be one which does not react to any appreciable extent with either the reactants or products of said reaction. The preferred solvents are anhydrous, aprotic solvents such as tetrahydrofuran, acetonitrile, chloroform, benzene or a tertiary amine which acts as solvent and proton acceptor, e.g., pyridine, When the acylating agent is an anhydride it may also be employed as the solvent without markedly affecting the course of the reaction.

At least two moles of the acylating agent per mole of the aminopyridine carboxylic acid should be employed. Lesser amounts usually result in a poorer yield of product or product which is contaminated with starting material. When the acid halide is used as the acylating agent, and the reaction solvent is not a tertiary amine, a tertiary amine, such as triethylamine or pyridine, corresponding in molar amount to the acid halide is added to act as a scavenger for the hydrogen halide formed.

Although the initial contacting of the reactants is carried out at ice-bath to ambient temperatures, in order to reduce the incidence of by-products, it is desirable after a few minutes of mixing to heat the reaction mixture from 50°–100° C. until the reaction is complete or nearly complete. The reaction time, which will vary depending on temperature, concentration and inherent reactivity of the starting reagents, is usually 1–72 hrs.

Occasionally, it is convenient to employ the acid addition salt of the aminopyridine carboxylic acid or a basic salt thereof as the starting material. When the acid addition or basic salt is employed, it is desirable to first neutralize with an equivalent amount of a base or acid, respectively, before adding the other reagents.

The intermediate product resulting from the above-described reaction is the corresponding 2-substituted-pyridooxazine-4(3H)-one. It is preferred that this intermediate be converted to the final product without isolation or characterization, by treatment with ammonia.

Experimentally, ammonia can be bubbled into the reaction mixture or, if the acyl anhydride has been employed as a solvent, the excess anhydride is removed and a suitable solvent added, followed by the addition of ammonia. The reaction of the intermediate with ammonia is generally complete within a few hours at the reflux temperature of the solvent selected. The basicity of the ammonia is frequently adequate to convert the acylaminopyridinecarboxamide, which is generated in situ, to the final products of the instant invention, but to insure the completeness of this conversion, the reaction solvent is removed and the residue treated with a dilute aqueous solution of sodium or potassium hydroxide. The desired product is obtained by acidification of the aqueous base with a suitable acid followed by suction filtration of the precipitated solid.

As one skilled in the art can readily appreciate, other dehydrating agents such as sulfuric acid, polyphosphoric acid or even heat alone can be employed to effect this cyclization of the intermediate acylaminopyridinecarboxamides to the final products.

The first alternate route to the products of the present invention is illustrated below for the preparation of 2-substituted-pyrido[2,3-d]pyrimidin-4(3H)-ones of formula I, although it is equally applicable to the synthesis of the compounds of formulae II and III.

form. When an acid halide is employed as the acylating agent is is desirable to add an equivalent of a tertiary amine to serve as a scavenger for the hydrogen halide generated during the reaction. Alternately, two moles of aminopyridinecarboxamide can be used, one acting as the substrate for acylation and the second to react with the acid formed.

After the acylation is complete, usually requiring several hours at 75°–100° C., the mixture is filtered from any insolubles and the filtrate concentrated to dryness. The residual intermediate is treated with dilute aqueous base and worked up according to the previously mentioned reaction procedure.

The second alternate synthetic scheme leading to the products of the present invention is again illustrated with the formation of compounds of formula I, but is equally applicable to the preparation of compounds of formulae II and III.

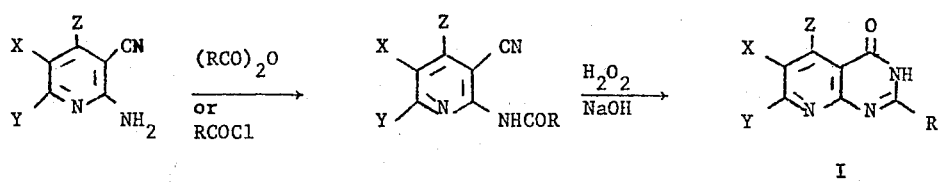

Experimentally, the requisite aminocyanopyridine, wherein X, Y and Z are as previously noted, is acylated with the appropriate acid anhydride or halide. As in previous schemes, a molar amount of a suitable tertiary amine is employed as a scavenger when said acid halide is the acylating agent.

The reaction is most conveniently carried out in a reaction-inert solvent such as acetonitrile, tetrahydrofuran or chloroform, employing an equimolar amount of amine and acylating agent with as much as a 100–200% excess of the latter. Reaction time is not critical, the reaction being complete or near complete in several hours at ambient temperatures. The intermediate acylaminocyanopyridine is most easily isolated by removal of the solvent and trituration of the residue with water.

The conversion of the intermediates to the final products of the present invention entails partial hydrolysis of the cyano moiety to a carboxamide and spontaneous cyclization to the desired products. Dilute aqueous hydrogen peroxide in dilute aqueous sodium hydroxide at temperatures of 50°–70° C. for a few minutes to several hours are adequate to effect this conversion. The product is isolated by acidification of the reaction mixture followed by filtration of the solids. The starting materials leading to the products of the instant invention are known in the literature, are prepared by modification of literature procedures, or are synthesized by processes which are also the subject of this invention.

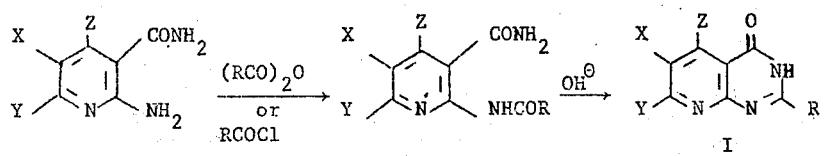

In practice, the aminopyridinecarboxamide, wherein X, Y and Z are as previously indicated, is contacted with an acid anhydride or halide in a reaction-inert solvent such as acetonitrile, tetrahydrofuran or chloroform.

For example, the halogenated acids, anhydrides and acid chlorides are prepared by the methods as taught by Henne, et al., *J. Am. Chem. Soc.*, 69, 281 (1947), England, et al., *J. Am. Chem. Soc.*, 80, 6442 (1958) and Wagner and Zook, "Synthetic Organic Chemistry," John Wiley & Sons, Inc., New York, New York, 1953, chapter 18, page 558 and chapter 17, page 546. 2-Aminonicotinic acid and its derivatives are synthesized according to the procedures of Taylor, et al., *J. Org. Chem.*, 19, 1633 (1954), Dornow, et al., *Chem. Ber.*, 84, 296 (1951), *Chem. Ber.*, 73, 542 (1940) and *Arch. Pharm.*, 290, 20 (1951) and Webb, et al., *J. Am. Chem. Soc.*, 66, 1456 (1944). 4-Aminonicotinic acid and the derivatives thereof are prepared by the procedures of Fox, *J. Org. Chem.*, 17, 547 (1952) and Wang, et al., *Tetrahedron*, 27, 2581 (1971).

The novel compounds of the present invention have been found to be highly effective herbicides and may be applied to the soil before emergence of the weeds, i.e., pre-emergence herbicides and may also be applied as post-emergence herbicides to weeds already growing in the soil. The preferred compounds of the present invention are 2-trifluoromethyl-6-chloropyrido[2,3-d]-pyrimidin-4(3H)-one, 2-(1,1,2,2-tetrafluoroethyl)-6-chloropyrido[2,3-d]-pyrimidin-4(3H)-one, 2-t-butyl-6-chloropyrido[2,3-d]pyrimidin-4(3H)-one and 2-t-butyl-6-i-propylpyrido[2,3-d]pyrimidin-4(3H)-one and 2-t-butyl-6-i-propylpyrido[2,3-d]pyrimidin-4(3H)-one.

Except for the salts, the compounds of the present invention are only slightly water-soluble. For post-emergence application, it is necessary that the herbicides penetrate the waxy integument that covers the surface parts of the weeds. Consequently, it is preferred not to use the water-soluble salts for post-emergence application since these compounds will easily wash off the surface of the weeds. The water-soluble organic compounds or their alkylamine salts, on the other hand, more readily penetrate the waxy integument and are therefore preferred for post-emergence application. The term alkylamine as employed in the instant invention is meant to encompass mono-, di- and trialkyl amines wherein the alkyl portion contains from 1 to 12 carbon atoms. The preferred alkylamine salts include those formed from dodecylamine and N,N-dimethyl-dodecylamine.

Because of the need to penetrate the waxy plant integument, it is generally preferred to apply the water-insoluble compounds or their alkylamine salts of the present invention in the form of a lipophilic phase. This can be readily accomplished by dissolving these compounds or their alkylamine salts in water-immiscible organic solvents such as xylene, kerosene or heavy aromatic naphthas, and apply the resultant solutions directly to the weeds. It is frequently desirable to employ isophorone or isopropanol as cosolvents. Alternatively, under certain circumstances, it might be desirable to employ aqueous emulsions or dispersions of these water-immiscible solutions.

For pre-emergence application it is, of course, necessary that the herbicides persist in the soil for a period of time. For this reason, simple water-soluble compounds would not be very effective. However, it has been found, substantial amounts of the water-soluble salts of the compounds of the present invention, after a period of time, will hydrolyze to the water-insoluble free acid form upon contact with the soil. Accordingly, aqueous solutions of the salts of the present invention can be conveniently used for pre-emergence application. The preferred salts for the aforementioned use include the alkali metal salts, especially the sodium and potassium salts.

For both pre- and post-emergence application, the compounds of the present invention or the aforementioned salts thereof may be applied directly or in the form of solutions, suspensions, emulsions, wettable powders (plus oil), flowable powders, dusts, sprays or aerosols. Solutions of the water-soluble compounds or their salts may be prepared from the aforementioned hydrocarbon solvents and such cosolvents as alkanols and ketones. Suspensions or dispersions of the compounds can readily be prepared by suspending the compounds in water with the aid of a wetting or dispersing agent such as the Tweens (polyoxyalkylene derivatives of sorbitan monolaurate), or alternately by dissolving them in a suitable solvent which can then be dispersed in water.

The compounds can also be applied as powders or dust by mixing them or milling them with such inert carriers as talc, diatomaceous earth, Fuller's earth, kaolin and various other clays. Aerosols containing the compounds of the present invention can also be prepared.

For pre-emergence herbicides, the dosage level will vary from ¼ to 10 pounds per acre, the exact amount depending upon the compound under consideration and the particular weed. For post-emergence herbicides, application on a level of ⅛ to 5 pounds per acre is usually adequate.

The first process of the present invention leads to the preparation of 2-aminonicotinonitrile, a compound useful as an intermediate for the synthesis of the herbicidal products of the present invention. The process for preparing 2-aminonicotinonitrile comprises (1) contacting equimolar proportions of a 1,1,3,3-tetraalkoxypropane wherein said alkoxy group contains from 1 to 4 carbon atoms with malononitrile in the presence of at least three molar equivalents of an alkanoic acid anhydride wherein said alkanoic acid contains from 2 to 4 carbon atoms at 30° to 200° C.; and (2) thereafter, contacting the intermediate 1-alkoxy-4,4-dicyano-1,3-butadiene product with equimolar proportions of ammonia at 25°–100° C.

In the initial step of the above-described reaction, although a solvent is not required, it is frequently desirable to employ an excess of the anhydride for this purpose.

Reaction temperatures are not critical, but it is preferred that the condensation be carried out at elevated temperatures. Although the preferred temperature ranges are from 50°–150° C., the temperatures below 50° C. will allow the reaction to proceed but at a much slower rate, while those above 150° C. lead to more undesirable by-products and offer no particular advantage.

Reaction time, as one skilled in the art readily appreciates, is a function of temperature, concentration and inherent reactivity of the reactants and, in general, varies from 12 to 72 hours. It has been further discovered that the use of a catalyst such as a Lewis acid, and in particular zinc chloride, can also markedly reduce the reaction time necessary to bring the reaction to completion or near-completion. When such a catalyst is employed, the reaction proceeds at a rate which allows work-up in 2 to 4 hours.

By catalytic amounts of the above-mentioned Lewis acids are contemplated quantities less than an equivalent amount and, further, quantities as small as 2.5 mole percent. A preferred range of 2.5 to 10 mole percent of such Lewis acids as zinc chloride, aluminum chloride or boron trifluoride provides a remarkable catalytic effect in the aforedescribed condensation.

Isolation of the intermediate 1-alkoxy-4,4-dicyano-1,3-butadiene can be achieved after removal of most of the excess anhydride by either dilution with water followed by filtration of the solids, or by distillation.

The aforementioned butadiene is preferably contacted with ammonia in a solvent such as methanol, chloroform, tetrahydrofuran, benzene or acetonitrile, or alternately, after the above-mentioned reaction mixture has been concentrated in volume, ammonia dissolved in an aqueous solution can be added to the reaction mixture. This latter variation of the present process obviates the necessity for the isolation and purification of the butadiene intermediate.

When a non-aqueous solvent is employed as the contact phase for the reaction of the butadiene and ammonia, said ammonia can be bubbled into the reaction solution or aqueous ammonium hydroxide, ammonia dissolved in an aqueous solution, can be added.

Although the quantity of ammonia needed by theory is one molar equivalent, it is preferred that a 5 to 50 fold excess be employed.

In general, it is further preferred that the reaction be heated from about 30° to about 75° C., said reaction temperatures requiring from 2 to 12 hours reaction time.

The product of the instant process, 2-aminonicotinonitrile, is isolated by concentration of the reaction mixture volume followed by trituration of the residue with an appropriate solvent and filtration.

The especially preferred embodiment of the present process, leading to the preparation of 2-aminonicotinonitrile, comprises the condensation of 1,1,3,3-tetramethoxypropane with malononitrile in the presence of acetic anhydride and a catalytic amount of zinc chloride at 50°–150° C., and thereafter reacting the intermediate 1-methoxy-4,4-dicyano-1,3-butadiene with ammonia at about 30° to about 75° C.

The starting reagents for the aforementioned reaction leading to the preparation of 2-aminonicotinonitrile are either commercial reagents or are prepared by reactions well known to those skilled in the art.

The second process of the instant invention is for preparing 2-aminonicotinonitriles of the formula:

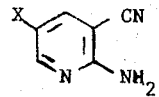

which process comprises (1) contacting a compound of the formula

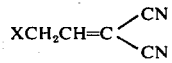

wherein X is alkyl containing from 1 to 4 carbon atoms with equimolar proportions of a trialkyl orthoformate wherein said alkyl contains from 1 to 4 carbon atoms, in the presence of at least two molar equivalents of an alkanoic anhydride wherein said alkanoic acid contains from 2 to 4 carbon atoms at 75°–175°C., and (2) thereafter, contacting the intermediate 1-alkoxy-2-alkyl-4,4-dicyano-1,3-butadiene product with equimolar proportions of ammonia at 25°–150° C.

In theory, the initial reaction of the above process employs an equimolar amount of the 1,1,-dicyanoalkylene and trialkyl orthoformate, but as much as a 100% excess of the latter reagent can be employed.

Although the reaction can be effected neat, it is preferred that a solvent be employed, usually an excess of the alkanoic anhydride.

The reaction, for practical reasons, is best conducted at elevated temperatures, frequently the reflux temperature of the reaction mixture, preferably at from 100°–150° C. Reaction temperatures above and below this range are also considered to be operable in providing the desired product. At the aforementioned temperatures, the reaction time will vary from 12 to 24 hours. It has also been unexpectedly discovered that Lewis acids, and especially zinc chloride will facilitate this condensation when employed in catalytic amounts, thus allowing a reduction in the reaction time to about 4 to 8 hours.

By catalytic amounts are contemplated quantities less than an equivalent amount, and, further, amounts as small as 2.5 mole percent. A preferred range of 2.5–20 mole percent of such Lewis acids as zinc chloride, aluminum chloride or boton trifluoride provides an unexpected catalytic effect in the aforedescribed condensation.

Although it is preferred, for reasons of economy, not to isolate and purify the intermediate product, the subsequent condensation of said intermediate with ammonia is preceded by removal of any excess alkanoic anhydride under reduced pressure.

The residual 1-alkoxy-2-alkyl-4,4-dicyano-1,3-butadiene is contacted with ammonia, preferably in a reaction-inert solvent such as acetonitrile, tetrahydrofuran, chloroform or a lower alkanol. Although only equimolar proportions of ammonia are needed, in practice, an excess of ammonia is generally bubbled through a solution of intermediate in an appropriate solvent for a period of time necessary to saturate the solution. It is further preferred that the reaction mixture be heated to the reflux temperature of the solvent in order to complete the reaction in a reasonable period of time.

Isolation of the product is facilitated by removal of the solvent in vacuo followed by trituration of the residual product with a suitable solvent, followed by filtration.

The especially preferred embodiment of the aforedescribed process leading to the synthesis of 2-amino-5-alkylnicotinonitriles comprises the condensation of a 1,1-dicyanopropylene of the formula $XCH_2CH=(CN)_2$, wherein X is methyl or i-propyl, with triethyl orthoformate in the presence of acetic anhydride at about 100° to about 150° C., and thereafter reacting the intermediate 1-ethoxy-2-alkyl-4,4-dicyano-1,3-butadiene of the formula $C_2H_5OCH=C(X)—CH=C(CN)_2$, wherein X is methyl or i-propyl, with ammonia. It is further preferred that said initial condensation employing the triethyl orthoformate be carried out in the presence of the Lewis acid and zinc chloride.

The starting materials for the above-described process are either available commercially or can be prepared by literature procedures. For example, the alkylidene malononitriles of the formula $XCH_2CH=C(CN)_2$ are synthesized according to the procedure as taught by Cope, et al., *J. Am. Chem. Soc.*, 63, 733 (1941), while the trialkyl orthoformates are prepared by the method of Mochel, et al., *J. Am. Chem. Soc.*, 70, 2268 (1948).

11

Also considered within the scope of the instant process is the condensation of 1,1-dicyanopropylenes of the formula $XCH_2C(X)=C(CN)_2$ wherein X is hydrogen or alkyl of 1 to 4 carbon atoms, with trialkyl orthoalkanoates of the formula $XCH(O-alkyl)_3$, wherein X is hydrogen or alkyl of 1 to 4 carbon atoms, in the presence of an alkanoic anhydride, conducted in the absence or presence of a Lewis acid, and thereafter contacting the intermediate of the formula (alkyl-O)—C(X)=C(X)—C(X)=C(CN)$_2$ with ammonia to provide the synthesis of 2-amino-4,5,6-trialkyl-nicotinonitriles.

The following examples are provided to illustrate further the scope of the present invention, and should not be construed as limitations thereof.

EXAMPLE 1

2-Trifluoromethyl-6-chloropyrido[2,3-d]pyrimidin-4(3H)-one (I; R = CF$_3$, X = Cl, Y and Z = H)

To 500 ml. of trifluoroacetic anhydride, cooled in an ice bath, is added in portions over a 10–15 min. period 50 g. (0.29 mole) of 2-amino-5-chloronicotinic acid, and the solution allowed to stir in the cold for 20 min. The cooling bath is removed, and the reaction mixture is heated at 55° C. under a nitrogen atmosphere for 65 hrs. The excess anhydride is removed under reduced pressure, the final traces of water and anhydride being removed by codistillation with benzene (60 ml.) and then diethyl ether (50 ml.), and the solid residue maintained under vacuum for 30 min.

The residue is dissolved in 1.6 l. of diethyl ether, and ammonia gas is bubbled into the resulting solution for 30 min. The precipitate which forms is filtered, washed with ether, dried (86.2 g.) and added to 300 ml. of cold (15° C.) 1N aqueous sodium hydroxide. Dissolution of the solids gradually takes place, followed by the formation of a precipitate, which is filtered. Addition of 300 ml. of 1N sodium hydroxide solution to the filtrate results in the formation of more solids which are filtered and combined with the first batch. The combined solids are dissolved in 1.5 l. of methanol and the resulting hazy solution treated with concentrated hydrochloric acid until a pH of approximately 1.1 is achieved (~15–20 ml. of 12N HCl). The precipitate is filtered, partially dried in vacuo and dissolved in warm acetone. The acetone solution is dried over sodium sulfate, concentrated to dryness and the residual solid triturated with hexane and filtered, 23.4 g., m.p. 239°–239.5° C. Additional material is obtained by partial evaporation of the acidified methanol filtrate and combined with the first crop. Recrystallization provides the analytical sample, m.p. 239°–240° C.

Anal. Calc'd for C$_8$H$_3$ON$_3$ClF$_3$: C, 38.49; H, 1.21; N, 16.83. Found: C, 38.81; H, 1.57; N, 16.79.

EXAMPLE 2

Starting with the requisite reagents and employing the procedure of Example 1, the following products are synthesized:

| Product | m.p., °C. | Formula |
|---|---|---|
| [Br-substituted pyrido[2,3-d]pyrimidinone with CF$_3$] | 248–250 | C$_8$H$_3$ON$_3$BrF$_3$ |
| [pyrido[2,3-d]pyrimidinone with CF$_3$] | 270–272 | C$_8$H$_4$ON$_3$F$_3$ |
| [dichloro pyrido[2,3-d]pyrimidinone with CF$_3$] | 220–222 | C$_8$H$_2$ON$_3$Cl$_2$F$_3$ |
| [dibromo pyrido[2,3-d]pyrimidinone with CF$_3$] | 241–242 | C$_8$H$_2$ON$_3$Br$_2$F$_3$ |
| [chloro pyrido[2,3-d]pyrimidinone with CF$_3$] | 208–209 | C$_8$H$_3$ON$_3$ClF$_3$ |

EXAMPLE 3

2-Pentafluoroethyl-6-bromopyrido[2,3-d]pyrimidin-4(3H)-one (I; R = —CF$_2$CF$_3$, X = Br, Y and Z = H).

A slurry comprising 2.69 g. (12.4 m moles) of 2-amino-5-bromonicotinic acid in 60 ml. of tetrahydrofuran and 60 ml. of acetonitrile containing 3.74 g. (37.1 m moles) of triethyl amine is stirred at room temperature while 6.75 g. (37.1 m moles) of perfluoropropionyl chloride is bubbled into the reaction mixture. The reaction is heated to reflux for 1.5 hrs., cooled to room temperature and ammonia gas bubbled through the mixture for 1.5 hrs. Reflux is then continued for 18 hrs. Inorganic salts are filtered from the cooled reaction mixture, and the residual oil, which remains on evaporation of the filtrate, is treated with 100 ml. of diethyl ether. More inorganic salts are filtered, and the filtrate subsequently concentrated to an oil. Water (15 ml.) is added to the residual oil, and the mixture is stirred while sufficient 6N hydrochloric acid is slowly added to provide a pH of 1.0. The resulting solid is collected by filtration, washed several times with water and dried in vacuo, 534 mg., m.p. 200°–202° C.

Mass Spectrum:Calc'd M$^+$: 344. Found: 344.

EXAMPLE 4

Employing the procedure of Example 3, and starting with the appropriate chemical reagents, the following analogs are prepared:

2-pentafluoroethyl-6-chloropyrido[2,3-d]pyrimidin-4(3H)-one (I, R = —CF$_2$CF$_3$, X = Cl, Y and Z = H), m.p. 198°–200° C.;

2-pentafluoroethylpyrido[2,3-d]pyrimidin-4(3H)-one (I; R = —CF$_2$CF$_3$, X, Y and Z = H), m.p. 196°–198° C.;

2-t-butylpyrido[2,3-d]pyrimidin-4(3H)-one (I; R = —C(CH$_3$)$_3$, X, Y and Z = H), m.p. 218°–220° C.

EXAMPLE 5

The procedure of Example 3 is again repeated, starting with the requisite intermediates, to provide the following congeners:

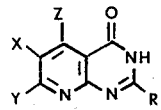

| Y | X | Z | R |
|---|---|---|---|
| H— | H— | H— | —CF₂CH₃ |
| H— | H— | H— | —CF₂CHF₂ |
| H— | H— | H— | —CF₂CHCl₂ |
| H— | Cl— | H— | —CF₂CH₃ |
| H— | Cl— | H— | —CF₂CCl₃ |
| H— | Cl— | H— | —CF₂CF₂Cl |
| H— | Br— | H— | —CF₂CHF₂ |
| H— | Br— | H— | —CF₂CF₂Cl |
| H— | Br— | H— | —CF₂CCl₃ |
| H— | CH₃— | H— | —CF₂CH₃ |
| H— | CH₃— | H— | —CF₂CF₃ |
| H— | CH₃— | H— | —CF₂Cl |
| H— | CH₃— | H— | —CF₂CCl₃ |
| H— | C₂H₅— | H— | —CF₂CF₂H |
| H— | C₂H₅— | H— | —CF₂CFClH |
| H— | C₂H₅— | H— | —CF₂CCl₂F |
| H— | n-C₃H₇— | H— | —CF₂CF₃ |
| H— | n-C₃H₇— | H— | —CF₂Cl |
| H— | n-C₃H₇— | H— | —CF₂CF₂H |
| H— | i-C₃H₇— | H— | —CF₂CF₂H |
| H— | i-C₃H₇— | H— | —CF₂CH₃ |
| H— | t-C₄H₉— | H— | —CF₂CF₃ |
| H— | t-C₄H₉— | H— | —CF₂CF₂Cl |
| H— | s-C₄H₉— | H— | —CF₂CHCl₂ |
| H— | s-C₄H₉— | H— | —CF₂Cl |
| H— | n-C₄H₉— | H— | —CF₂Cl |
| H— | n-C₄H₉— | H— | —CF₂CF₃ |
| H— | n-C₄H₉— | H— | —CHF₂ |

EXAMPLE 6

2-Chlorodifluoromethylpyrido[2,3-d]pyrimidin-4(3H)-one (I; R = CF₂Cl, X, Y and Z = H)

To a slurry of 2.74 g. (0.02 mole) of 2-aminonicotinamide in 100 ml. of tetrahydrofuran, under a nitrogen atmosphere and cooled to 5° C. in an ice bath, is added dropwise 3.3 g. (22.5 m moles) of chlorodifluoroacetyl chloride in 20 ml. of the same solvent. The reaction mixture is heated to reflux for 2 hrs., cooled, and the solids, consisting mostly of 2-aminonicotinamide hydrochloride, are filtered. Evaporation of the filtrate in vacuo provides the crude intermediate product, which is triturated with diethyl ether and filtered, 1.02 g., m.p. 187°–189° C.

One gram of the intermediate is slurried in 7 ml. of cold 1N sodium hydroxide for 5 min., and the hazy suspension subsequently filtered. The filtrate is acidified with 6N hydrochloric acid, and the resulting precipitate filtered, washed with water and dried, 379 mg., m.p. 219°–221° C.

Anal. Calc'd for C₈H₆O₂N₃ClF₂: C, 41.49; H, 1.74; N, 18.14. Found: C, 41.79; H, 2.05; N, 18.75.

EXAMPLE 7

Following the procedure of Example 6, and employing the requisite starting materials, the congeners noted below are prepared:

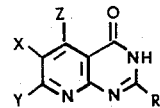

| Y | X | Z | R | m.p., °C. |
|---|---|---|---|---|
| H— | H— | H— | —CF₂CHFCl | 149–151 |
| H— | Cl— | H— | —CF₂Cl | 219–220 |
| H— | Cl— | H— | —CF₂CHFCl | 176–178 |
| H— | Cl— | H— | —CF₂CF₂H | 203–204 |
| H— | Br— | H— | —CF₂Cl | 229–230 |
| H— | Br— | H— | —CF₂CFClH | 182–183 |
| H— | Br— | H— | —CF₂CF₂H | 214–215 |
| CH₃— | CH₃— | H— | —CF₂CFClH | 201–204 |
| CH₃— | Cl— | H— | —CF₂CFClH | 216–218 |
| H— | H— | H— | —CF₂CF₂H | 165–168 |
| H— | Cl— | H— | —CH(CH₃)CH₂CH₃ | 222–224 |
| H— | Cl— | H— | —CH₂CH₂CH₂CH₃ | 204–206 |
| H— | Cl— | H— | —CH(CH₃)₂ | 254–256 |
| H— | Cl— | H— | —CH₂CH(CH₃)₂ | 216–217 |
| H— | H— | H— | —C(CH₃)₃ | 219–220 |

EXAMPLE 8

The procedure of Example 6 is again repeated, employing the appropriate starting materials, to provide the following products:

| Y | X | Z | R |
|---|---|---|---|
| H— | H— | H— | —CH₂CH₂CH₃ |
| H— | H— | H— | -cyclo C₄H₇ |
| H— | H— | H— | —CH₂CH₂CH(CH₃)₂ |
| H— | Br— | H— | —CH(CH₃)CH₂CH₃ |
| H— | Br— | H— | —CH(CH₃)₂ |
| H— | Br— | H— | —C(CH₃)₃ |
| H— | Br— | H— | -cyclo C₃H₅ |
| H— | Cl— | H— | -cyclo C₃H₅ |
| H— | Cl— | H— | —(CH₂)₄CH₃ |
| H— | Cl— | H— | -cyclo C₅H₉ |
| H— | Cl— | H— | —CH(C₂H₅)₂ |
| CH₃— | H— | CH₃— | —CF₃ |
| CH₃— | H— | CH₃— | —CF₂CF₂H |
| CH₃— | H— | CH₃— | —CF₂CFClH |
| CH₃— | H— | CH₃— | —CF₂CF₂Cl |
| CH₃— | H— | CH₃— | —CH(CH₃)₂ |
| CH₃— | H— | CH₃— | —CH₂CH(CH₃)₂ |
| CH₃— | H— | CH₃— | -cyclo C₃H₅ |
| CH₃— | CH₃— | H— | —CF₃ |
| CH₃— | CH₃— | H— | —CF₂CH₃ |
| CH₃— | CH₃— | H— | —CF₂CF₃ |
| CH₃— | CH₃— | H— | —CH(CH₃)CH₂CH₃ |
| H— | CH₃— | CH₃— | —CF₂Cl |
| H— | CH₃— | CH₃— | —CF₂CF₃ |
| H— | CH₃— | CH₃— | —CF₂H |
| CH₃— | Cl— | H— | —CF₂Cl |
| CH₃— | Cl— | H— | —CF₂CFClH |
| CH₃— | Cl— | H— | -cyclo C₅H₉ |
| H— | Cl— | CH₃— | —CF₂CF₃ |
| H— | Cl— | CH₃— | —CF₂CF₂H |
| H— | Cl— | CH₃— | —CF₂CH₃ |
| CH₃— | Br— | H— | —CF₂CF₂Cl |
| CH₃— | Br— | H— | —CH₂CH(CH₃) |
| CH₃— | Br— | H— | -cyclo C₄H₇ |
| CH₃— | Br— | H— | -cyclo C₅H₉ |
| CH₃— | Br— | H— | —(CH₂)₃CH₃ |
| H— | Br— | CH₃— | —CF₃ |
| H— | Br— | CH₃— | —CF₂Cl |
| H— | Br— | CH₃— | —CF₂CF₃ |
| H— | Br— | CH₃— | —CF₂CCl₃ |

EXAMPLE 9

2-Trifluoromethyl-5,7-dimethyl-6-chloropyrido[2,3-d]pyrimidin-4(3H)-one (I; R = CF₃, X = Cl, Y and Z = CH₃)

A solution of 1.2 g. (5.1 m moles) of 2-amino-4,6-dimethyl-5-chloronicotinic acid hydrochloride in 15 ml. of trifluoroacetic anhydride is heated to reflux for 22 hrs., and the excess anhydride subsequently evaporated in vacuo. The residual intermediate is taken up in 200 ml. of diethyl ether, filtered, and the filtrate treated with ammonia for 20 min. The resulting precipitate is filtered and dried, 1.8 g.

With stirring and cooling, 1.7 of the above intermediate is added to 4 ml. of conc. sulfuric acid and allowed to remain for 10–15 min., after which 20 ml. of 3N sodium hydroxide solution is added, and the resulting precipitate is filtered, washed with a small quantity of water and dried, 888 mg., m.p. 226°–228° C.

Mass Spectrum:Calc'd M$^+$: 277. Found: 277.

EXAMPLE 10

By a procedure similar to that of Example 9, 2-amino-4,6-dimethylnicotinic acid hydrochloride and trifluoroacetic anhydride provided 2-trifluoromethyl-5,7-dimethylpyrido[2,3-d]pyrimidin-4(3H)-one (I; R = $CF_3$, X = H, Y and Z = $CH_3$), m.p. 278°–280° C.

Anal. Calc'd for $C_{10}H_8ON_3F_3$: C, 49.63; H, 3.32; N, 17.29. Found: C, 48.90; H, 3.43; N, 17.45.

EXAMPLE 11

The procedure of Example 9 is repeated, starting with the requisite starting materials, to provide the following congeners:

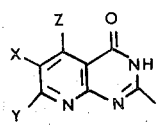

| Y | X | Z | R |
|---|---|---|---|
| $CH_3-$ | $Cl-$ | $CH_3-$ | $-CF_2CF_3$ |
| $CH_3-$ | $Cl-$ | $CH_3-$ | $-CF_2CF_2H$ |
| $CH_3-$ | $Cl-$ | $CH_3-$ | $-CF_2H$ |
| $CH_3-$ | $Cl-$ | $CH_3-$ | $-CF_2Cl$ |
| $CH_3-$ | $Cl-$ | $CH_3-$ | $-CF_2CHFCl$ |
| $CH_3-$ | $Cl-$ | $CH_3-$ | $-CH(CH_3)_2$ |
| $CH_3-$ | $Cl-$ | $CH_3-$ | $-CH_2CH(CH_3)_2$ |
| $CH_3-$ | $Cl-$ | $CH_3-$ | $-(CH_2)_4CH_3$ |
| $CH_3-$ | $Cl-$ | $CH_3-$ | -cyclo $C_3H_5$ |
| $CH_3-$ | $Cl-$ | $CH_3-$ | -cyclo $C_5H_9$ |
| $CH_3-$ | $Br-$ | $CH_3-$ | $-CF_3$ |
| $CH_3-$ | $Br-$ | $CH_3-$ | $-CF_2Cl$ |
| $CH_3-$ | $Br-$ | $CH_3-$ | $-CF_2CH_3$ |
| $CH_3-$ | $Br-$ | $CH_3-$ | $-CF_2CF_2H$ |
| $CH_3-$ | $Br-$ | $CH_3-$ | $-CF_2CFCl_2$ |
| $CH_3-$ | $Br-$ | $CH_3-$ | $-CF_2CF_2Cl$ |
| $CH_3-$ | $Br-$ | $CH_3-$ | $-CH_2CH(CH_3)_2$ |
| $CH_3-$ | $Br-$ | $CH_3-$ | $-CH(CH_3)CH_2CH_3$ |
| $CH_3-$ | $Br-$ | $CH_3-$ | $-CH_2C(CH_3)_3$ |
| $CH_3-$ | $Br-$ | $CH_3-$ | -cyclo $C_5H_9$ |
| $CH_3-$ | $CH_3-$ | $CH_3-$ | $-CF_3$ |
| $CH_3-$ | $CH_3-$ | $CH_3-$ | $-CF_2CF_3$ |
| $CH_3-$ | $CH_3-$ | $CH_3-$ | $-CF_2Cl$ |
| $CH_3-$ | $CH_3-$ | $CH_3-$ | $-CF_2CF_2H$ |
| $CH_3-$ | $CH_3-$ | $CH_3-$ | $-CF_2CF_2Cl$ |
| $CH_3-$ | $CH_3-$ | $CH_3-$ | $-CF_2CHFCl$ |
| $CH_3-$ | $CH_3-$ | $CH_3-$ | $-CH_2CH_2CH_3$ |
| $CH_3-$ | $CH_3-$ | $CH_3-$ | $-CH(CH_3)$ |
| $CH_3-$ | $CH_3-$ | $CH_3-$ | $-CH(CH_3)CH_2CH_3$ |
| $CH_3-$ | $CH_3-$ | $CH_3-$ | -cyclo $C_3H_5$ |
| $CH_3-$ | $CH_3-$ | $CH_3-$ | -cyclo $C_4H_7$ |

EXAMPLE 12

2-t-Butyl-6-chloropyrido[2,3-d]pyrimidin-4(3H)-one (I; R = $C(CH_3)_3$, X = Cl, Y and Z = H)

To a suspension of 25 g. (0.12 mole) of 2-amino-5-chloronicotinic acid hydrochloride in 300 ml. of dry pyridine, cooled in an ice-water bath, is added dropwise over a period of 35 min. 30 g. (0.25 mole) of pivaloyl chloride. When the addition is complete, the cooling bath is removed and the reaction mixture allowed to stir at room temperature for 40 min. and then at reflux temperature for 22 hrs.

The reaction is cooled to room temperature, the pyridine removed under reduced pressure and the residue stirred with 500 ml. of diethyl ether. After filtration of the pyridine hydrochloride, ammonia gas is bubbled through the ether filtrate for 15 min. The precipitated solid is filtered and discarded, and the residue, remaining after the filtrate is concentrated, is dissolved in 600 ml. of chloroform. Ammonia gas is bubbled through the solution for 1.25 hrs., and the white precipitate collected by filtration, 27.7 g. An additional crop of the intermediate product is obtained by concentration of the filtrate and trituration of the residue with 200 ml. of ether, 7.5 g.

A slurry of 35.2 g. of the above intermediate in 175 ml. of 5N sodium hydroxide solution is heated to reflux for 2.25 hrs. The mixture is cooled, and the sodium salt filtered, dissolved in 300 ml. of water and the pH adjusted from 11.5 to 2.5 by the addition of 12N hydrochloric acid. The product is filtered, washed with water (2 × 200 ml.) and dried, 18.2 g., m.p. 275°–276° C. A small sample is recrystallized from methanol for analysis.

Anal. Calc'd for $C_{11}H_{12}ON_3Cl$: C, 55.75; H, 6.10; N, 17.73. Found: C, 55.44; H, 6.61; N, 17.47.

EXAMPLE 13

The procedure of Example 12 is repeated, starting with the appropriate reagents, to provide the following compounds: 2-t-butyl-6-bromopyrido[2,3-d]pyrimidin-4(3H)-one; 2-t-butyl-5,7-dimethylpyrido[2,3-d]pyrimidin-4(3H)-one; 2-t-butyl-5,7-dimethyl-6-chloropyrido[2,3-d]pyrimidin-4(3H)-one; 2-t-butyl-5-methyl-6-chloropyrido[2,3-d]pyrimidin-4(3H)-one; 2-t-butyl-5-methyl-6-bromopyrido[2,3-d]pyrimidin-4(3H)-one; and 2-t-butyl-6-chloro-7-methyl-pyrido[2,3-d]-pyrimidin-4(3H)-one.

EXAMPLE 14

2-t-Butyl-6-methylpyrido[2,3-d]pyrimidin-4(3H)-one (I; R = $C(CH_3)_3$, X = $CH_3$, Y and Z = H)

A slurry consisting of 2-amino-5-methylnicotinonitrile (1.5 g.) and 2 ml. of triethylamine in 50 ml. of chloroform is treated with 2 ml. of pivaloyl chloride and 10 ml. of acetonitrile, and the resulting solution heated to reflux for 4 hrs. After standing overnight at room temperature the reaction mixture is treated with 50 ml. of a saturated sodium bicarbonate solution and the organic phase separated and washed with 1N hydrochloric acid. The chloroform layer is separated, dried over sodium sulfate and concentrated to near dryness. The precipitated solids, 2-pivaloylamino-5-methylnicotinonitrile, are collected in two crops and dried, 600 mg. and 700 mg.

The intermediate nitrile (1.3 g.) is slurried in 20 ml. of 5N sodium hydroxide followed by the addition of 5 ml. of 3% hydrogen peroxide and ~1 ml. of ethanol. The reaction mixture is then heated at steam bath temperatures for 4 hrs. and allowed to remain at room temperature for two days. The sodium salt of the desired product is filtered from the reaction, washed with acetonitrile and suspended in 20 ml. of water. Sufficient 12N hydrochloric acid is added to the suspension to provide a pH of 3, and the mixture is cooled in an ice bath. The product is filtered, dried and recrystallized from ethanol, 550 mg., m.p. 272°–274° C.

EXAMPLE 15

2-Trifluoromethyl-6-methylpyrido[2,3-d]pyrimidin-4(3H)-one (I; R = $CF_3$, X = $CH_3$, Y and Z = H)

Starting with 1.5 g. of 2-amino-5-methylnicotinonitrile and 1.0 ml. of trifluoroacetic anhydride, and following the procedure of Example 14, the desired product is isolated as a crystalline solid, 600 mg., m.p. 270°–272° C.

EXAMPLE 16

Employing the requisite starting materials and again repeating the procedure of Example 14, the following pyrido[2,3-d]pyrimidin-4(3H)-ones are synthesized:

| Y | X | Z | R |
|---|---|---|---|
| H— | $C_2H_5$— | H— | —$CF_3$ |
| H— | $C_2H_5$— | H— | —$CF_2CF_2H$ |
| H— | $C_2H_5$— | H— | —$CH(CH_3)_2$ |
| H— | $C_2H_5$— | $CH_3$— | —$CF_2Cl$ |
| $CH_3$— | $C_2H_5$— | $CH_3$— | —$CF_3$ |
| $CH_3$— | $C_2H_5$— | $CH_3$— | -cyclo $C_3H_5$ |
| $CH_3$— | $C_2H_5$— | $CH_3$— | —$CH_2CH(CH_3)_2$ |
| H— | n-$C_3H_7$— | H— | —$CF_2CHFCl$ |
| H— | n-$C_3H_7$— | H— | —$CF_2Cl$ |
| H— | n-$C_3H_7$— | H— | -cyclo $C_5H_9$ |
| $CH_3$— | n-$C_3H_7$— | H— | —$(CH_2)_4CH_3$ |
| $CH_3$— | n-$C_3H_7$— | $CH_3$— | —$CH_2CH(CH_3)_2$ |
| $CH_3$— | n-$C_3H_7$— | $CH_3$— | —$CF_2Cl$ |
| $CH_3$— | n-$C_3H_7$— | $CH_3$— | —$CF_2CH_3$ |
| H— | i-$C_3H_7$— | H— | —$C(CH_3)_3$ |
| H— | i-$C_3H_7$— | H— | —$CH(CH_3)$ |
| H— | i-$C_3H_7$— | H— | -cyclo $C_4H_7$ |
| $CH_3$— | i-$C_3H_7$— | $CH_3$— | —$CF_3$ |
| $CH_3$— | i-$C_3H_7$— | $CH_3$— | —$CF_2CF_2Cl$ |
| $CH_3$— | i-$C_3H_7$— | $CH_3$— | —$CF_2CF_3$ |
| H— | n-$C_4H_9$— | H— | —$C(CH_3)_3$ |
| H— | n-$C_4H_9$— | H— | —$CF_3$ |
| H— | n-$C_4H_9$— | H— | —$CF_2CF_2H$ |
| $CH_3$— | n-$C_4H_9$— | H— | -cyclo $C_3H_5$ |
| $CH_3$— | n-$C_4H_9$— | $CH_3$— | -cyclo $C_3H_5$ |
| $CH_3$— | n-$C_4H_9$— | $CH_3$— | —$CF_2H$ |
| H— | s-$C_4H_9$— | H— | —$(CH_2)_2CH(CH_3)_2$ |
| H— | s-$C_4H_9$— | H— | —$CF_3$ |
| H— | s-$C_4H_9$— | $CH_3$— | -cyclo $C_5H_9$ |
| $CH_3$— | s-$C_4H_9$— | $CH_3$— | —$CF_2CF_3$ |
| $CH_3$— | s-$C_4H_9$— | $CH_3$— | —$CF_2CCl_3$ |
| H— | t-$C_4H_9$— | H— | —$CF_3$ |
| H— | t-$C_4H_9$— | H— | —$CF_2CFCl_2$ |
| $CH_3$— | t-$C_4H_9$— | $CH_3$— | —$(CH_2)_4CH_3$ |
| $CH_3$— | t-$C_4H_9$— | $CH_3$— | —$C(CH_3)_3$ |
| $CH_3$— | t-$C_4H_9$— | $CH_3$— | —$CF_2CF_2H$ |

EXAMPLE 17

2-Trifluoromethylpyrido[4,3-d]pyrimidin-4(3H)-one (III; R = $CF_3$, $X_1$, Y and Z = H)

To a suspension of 2.39 g. (15.5 m moles) of ammonium 4-aminonicotinate in 40 ml. of tetrahydrofuran containing 2.44 g. (31 m moles) of dry pyridine, and cooled to 5° C. is added with stirring 9.75 g. (46.5 m moles) of trifluoroacetic anhydride in 5 ml. of the same solvent over a period of 10 min. The reaction mixture is stirred at room temperature for 20 min., and then heated to reflux for 30 min.

The reaction mixture is cooled to 2° C. employing an ice-water bath, and ammonia gas is passed through the solution at a moderate rate for 5 min. The mixture is heated again to reflux for 15 min., after which, a small amount of solids are filtered and the filtrate concentrated in vacuo to a small volume. A saturated sodium chloride solution (10 ml.) is added and the precipitated solids are filtered, washed with water (3 × 20 ml.) and dried, 1.4 g., m.p. 263°–265° C. A small sample is recrystallized from acetonitrile, m.p. 276°–278° C.

Mass Spectrum: Calc'd M⁺: 215. Found: 215.

EXAMPLE 18

The procedure of Example 17 is repeated, starting with the requisite reagents, to provide the following pyrido[4,3-d]pyrimidin-4(3H)-one congeners: 2-difluorochloromethyl-8-bromopyrido[4,3-d]pyrimidin-4(3H)-one; 2-pentafluoroethyl-5-methyl-8-chloropyrido[4,3-d]pyrimidin-4(3H)-one; 2-i-propyl-5,7-dimethylpyrido[4,3-d]pyrimidin-4(3H)-one; 2-(1,1,2,2-tetrafluoroethyl)-7-methyl-8-bromopyrido[4,3-d]pyrimidin-4(3H)-one; 2-cyclopentyl-8-chloropyrido-[4,3-d]pyrimidin-4(3H)-one; 2-s-butyl-8-bromopyrido[4,3-d]pyrimidin-4(3H)-one; 2-(1,1-difluoro-2,2,2-trichloroethyl)-5,7-dimethyl-pyrido[4,3-d]pyrimidin-4(3H)-one; 2-trifluoromethyl-5,7-dimethyl-8-chloropyrido[4,3-d]pyrimidin-4(3H)-one; 2-t-butylpyrido[4,3-d]pyrimidin-4(3H)-one; 2-cyclopropyl-8-bromopyrido[4,3-d]-pyrimidin-4(3H)-one; 2-n-pentyl-7-methyl-8-bromopyrido[4,3-d]pyrimidin-4(3H)-one; 2-difluoromethyl-7-methylpyrido[4,3-d]pyrimidin-4(3H)-one; and 2-(1,1-difluoro-2-chloroethyl)-8-chloropyrido[4,3-d]pyrimidin-4(3H)-one.

EXAMPLE 19

The procedure of Example 1 is again repeated, employing the appropriate starting chemical reagents, to provide the following pyrido[3,4-d]-pyrimidin-4(3H)-one analogs:

| $X_1$ | $X_2$ | R |
|---|---|---|
| H— | H— | —$CF_3$ |
| H— | H— | —$CF_2CF_3$ |
| H— | H— | —$CF_2Cl$ |
| H— | H— | —$CH_2CH(CH_3)_2$ |
| H— | H— | -cyclo $C_3H_5$ |
| Cl— | H— | —$CF_3$ |
| Cl— | H— | —$CF_2CF_2H$ |
| Cl— | H— | —$C(CH_3)_3$ |
| H— | Cl— | —$CF_2CF_3$ |
| H— | Cl— | —$CF_2CH_2Cl$ |
| H— | Cl— | —$CF_2Cl$ |
| Cl— | Cl— | -cyclo $C_5H_9$ |
| Cl— | Cl— | —$CH(CH_3)_2$ |
| Cl— | Cl— | —$(CH_2)_4CH_3$ |
| Br— | H— | —$CH(CH_3)CH_2CH_3$ |
| Br— | H— | -cyclo $C_4H_7$ |
| Br— | H— | —$CF_3$ |
| H— | Br— | —$CF_3$ |
| H— | Br— | —$CH_2CH(CH_3)_2$ |
| H— | Br— | — $CF_2CF_2H$ |
| Br— | Br— | —$CF_2CF_3$ |
| Br— | Br— | —$CF_2CHFCl$ |
| Br— | Br— | —$C(CH_3)_3$ |

-continued

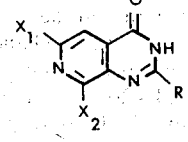

| X₁ | X₂ | R |
|---|---|---|
| Br— | Br— | -cyclo C₃H₅ |

EXAMPLE 20

2-Trifluoromethyl-6-chloropyrido[2,3-d]pyrimidin-4(3H)-one Ammonium Salt

Ammonia gas is slowly bubbled into a solution of 300 mg. of 2-trifluoromethyl-6-chloropyrido[2,3d]pyrimidin-4(3H)-one in 40 ml. of methanol cooled to 5° C. After 10 min. the gas inlet is removed and the methanol carefully removed in vacuo to provide the product as a white solid, 311 mg., m.p. 212°–225° C., with decomposition.

EXAMPLE 21

2-Trifluoromethyl-6-chloropyrido[2,3-d]pyrimidin-4(3H)-one N,N-dimethyldodecylamine Salt N,N-Dimethyldodecylamine (257 mg., 1.2 m moles) is added to a solution of 300 mg. (1.2 m moles) of 2-trifluoromethyl-6-chloropyrido[2,3-d]pyrimidin-4(3H)-one in 10 ml. of chloroform and the solution allowed to stir at room temperature for 20 min. The solvent is removed in vacuo, and the product is isolated as a clear oil, 546 mg.

Employing a similar procedure, and starting with the appropriate pyrido[2,3-d]-, pyrido[4,3-d]- or pyrido[3,4-d]pyrimidin-4(3H)-one and the requisite mono-, di- or trialkylamine, the amine salts of the subject compounds are suitably prepared.

EXAMPLE 22

2-(1,1,2,2-Tetrafluoroethyl)-6-chloropyrido[2,3-d]pyrimidin-4(3H)-one Sodium Salt To a solution of 400 mg. (10 m moles) of sodium hydroxide dissolved in 30ml. of methanol is added portionwise 2.8 g. (10 m moles) of 2-(1,1,2,2-tetrafluoroethyl)-6-chloropyrido[2,3-d]pyrimidin-4(3H)-one, and the resulting solution allowed to stir for several minutes. The solvent is removed under reduced pressure, and the residual solid product is triturated with ether, filtered and dried.

In a similar manner, starting with the requisite pyridopyrimidin-4(3)-one and alkali metal hydroxide, the alkali metal salts of the subject compounds are conveniently prepared.

EXAMPLE 23

2-Aminonicotinonitrile

A. 1-Methoxy-4,4-dicyano-1,3-butadiene

A solution of 2.0 g. (31 m moles) of malononitrile and 5 g. (31 m moles) of 1,1,3,3-tetramethoxypropane in 12 ml. of acetic anhydride is heated to reflux for 24 hrs. The reaction mixture is distilled separating the lower boiling by-products and solvent from the product. The product fraction is diluted with water and the resulting precipitate is filtered and recrystallized from isopropanol-water, 1.0 g., m.p. 74°–76° C.

B. 2-Aminonicotinonitrile

Ammonia gas is slowly bubbled into a methanol (10 ml.) solution of 500 mg. (3.7 m moles) of 1-methoxy-4,4-dicyano-1,3-butadiene until the solution is saturated. The gas flow is stopped, and the reaction mixture allowed to remain at room temperature overnight. The solvent is removed under reduced pressure, and the residual solid triturated with a small amount of isopropanol, filtered and dried, 100 mg., m.p. 130°–133° C. A small sample is purified by sublimation, m.p. 133°–134° C.

EXAMPLE 24

2-Aminonicotinonitrile (ZnCl₂ Catalyst)

A solution of 41 g. (0.25 mole) of 1,1,3,3-tetramethoxypropane in 5 l of acetic anhydride is treated portionwise with 1.5 g. (0.01 mole) of anhydrous zinc chloride, during which time the temperature of the solution rose to ~90° C. When the addition is complete, the temperature is raised and reflux temperatures are maintained while 9.2 g. (0.14 mole) of malononitrile in 10 ml. of acetic anhydride is added over a period of one hour. Refluxing is continued for 2.5 hrs., after which the solution is cooled and the volume of the reaction mixture concentrated 50% under reduced pressure. The residual content is transferred to a distillation apparatus and the fraction distilling at 122°–132°C./0.2 m m pressure is isolated, providing 7.0 g. of the desired intermediate.

To a solution of 2.68 g. (0.02 mole) of the above intermediate in 120 ml. of methanol is added 105 ml. of 30% aqueous ammonium hydroxide solution and the reaction mixture heated to reflux for 2 hrs. The solvent is removed in vacuo and the residue dissolved in 200 ml. of chloroform and treated with decolorizing charcoal. Removal of the solvent from the filtered solution, followed by trituration of the residue with petroleum ether-hexane provides 2-aminonicotinonitrile, 1.64 g., m.p. 131°–133° C., identical with that isolated in Example 23.

EXAMPLE 25

The procedure of Example 24 is followed employing 9.6 kg. of 1,1,3,3-tetramethoxypropane, 702 g. of zinc chloride, 2.2 kg. of malonitrile and 12.9 l. of acetic anhydride with the exception that at the end of the reflux period the reaction mixture is filtered and the filtrate concentrated at aspirator pressure and 50°C. until very little volatiles are collected. The residue is then treated with a total of 44 lbs. of 30% aqueous ammonium hydroxide solution without isolation of the intermediate butadiene.

Refluxing is continued for 30 min. following the addition of the aqueous ammonium hydroxide, and the reaction worked up in a manner similar to Example 24 wherein a total of 1.55 kg. of the 2-aminonicotinonitrile is isolated.

EXAMPLE 26

2-Aminonicotinonitrile is prepared by the procedure of Example 23, wherein the following 1,1,3,3-tetraalkoxypropanes are employed in place of 1,1,3,3-tetramethoxypropane in the Example 23A procedure:

(n-C₃H₇0)₂CHCH₂CH(O-n-C₃H₇)₂
(i-C₃H₇0)₂CHCH₂CH(O-i-C₃H₇)₂
(s-C₄H₉O)₂CHCH₂CH(O-s-C₄H₉)₂
(n-C₄H₉0)₂CHCH₂CH(O-n-C₄H₉)₂
(i-C₄H₉0)₂CHCH₂CH(O-n-C₄H₉)₂

EXAMPLE 27

2-Aminonicotinonitrile is again prepared by the procedure of Example 23, employing the requisite starting reagents with the substitution of the following combination of alkanoic acid anhydride and 1,1,3,3-tetraalkoxypropane in place of acetic anhydride and 1,1,3,3-tetramethoxypropane:

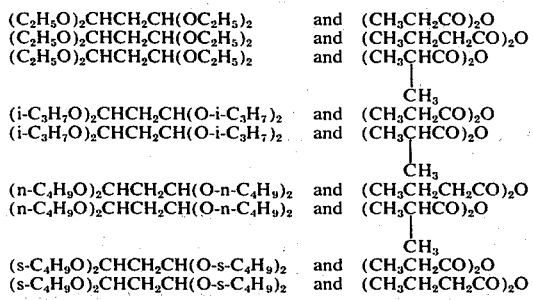

EXAMPLE 28

2-Amino-5-methylnicotinonitrile

To propylidene malonitrile, formed via the condensation of 29.0 g. (0.5 mole) of propionaldehyde with 39.6 g. (0.5 mole) of malonitrile according to the procedure of Cope, et al., *J. Am. Chem. Soc.*, 63, 733 (1941), is added 250 ml. of acetic anhydride and 50 ml. of triethyl orthoformate and the resulting solution heated to reflux for 18 hrs. The reaction mixture is concentrated in vacuo, and the residual oily intermediate taken up into 250 ml. of acetonitrile. Ammonia gas is bubbled through the solution for 1.5 hrs., and the reaction mixture subsequently heated to reflux for 3 hrs. The solvent is removed from the filtered solution under reduced pressure, and the partially solidified residue triturated with diethyl ether. The crude product is filtered and recrystallized from a small volume of isopropanol.

EXAMPLE 29

The general procedure of Example 28 is repeated, wherein 2.0 g. of propylidene malononitrile, 5 ml. of triethyl orthoformate and 500 mg. of zinc chloride is added to 21 ml. of acetic anhydride and the resulting solution heated on a steam bath for 45 min. and then at reflux temperatures for 6 hrs. The reaction is stripped in vacuo to heavy oil which is dissolved in 15 ml. of chloroform into which is bubbled dry ammonia for 30 min. The solution is heated to reflux for one hour, filtered and concentrated to a partially crystallized oil. Trituration with a small amount of ethanol, followed by filtration provides the desired product, m.p. 166°–168° C.

EXAMPLE 30

The procedure of Example 29 is repeated, employing the requisite trialkyl orthoformate, alkylidene molononitrile, alkanoic acid anhydride and catalyst, to provide the indicated products:

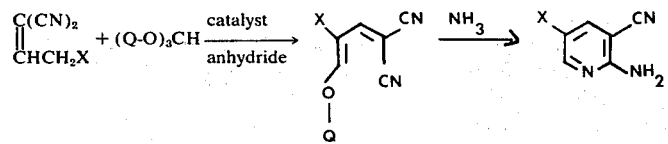

| X | Q | catalyst | anhydride | X |
|---|---|---|---|---|
| CH₃— | CH₃— | ZnCl₂ | (CH₃CO)₂O | CH₃— |
| CH₃— | C₂H₅— | BF₃ | (CH₃CO)₂O | CH₃— |
| CH₃— | n-C₄H₉— | BF₃ | (CH₃CH₂CO)₂O | CH₃— |
| C₂H₅— | CH₃— | AlCl₃ | (CH₃CH₂CH₂CO)₂O | C₂H₅— |
| C₂H₅— | i-C₃H₇— | ZnCl₂ | (CH₃CH₂CH₂CO)₂O | C₂H₅— |
| C₂H₅— | C₂H₅— | ZnCl₂ | (CH₃CO)₂O | C₂H₅— |
| C₂H₅— | s-C₄H₉— | AlCl₃ | (CH₃CO)₂O | C₂H₅— |
| n-C₃H₇— | C₂H₅— | ZnCl₂ | (CH₃CO)₂O | n-C₃H₇— |
| n-C₃H₇— | n-C₃H₇— | BF₃ | (CH₃CHCO)₂O \| CH₃ | n-C₃H₇— |
| i-C₃H₇— | CH₃— | ZnCl₂ | (CH₃CO)₂O | i-C₃H₇— |
| i-C₃H₇— | C₂H₅— | BF₃ | (CH₃CO)₂O | i-C₃H₇— |
| i-C₃H₇— | n-C₃H₇— | BF₃ | (CH₃CO)₂O | i-C₃H₇— |
| i-C₃H₇— | n-C₄H₉— | AlCl₃ | (CH₃CH₂CO)₂O | i-C₃H₇— |
| i-C₃H₇— | n-C₄H₉— | ZnCl₂ | (CH₃CH₂CO)₂O | i-C₃H₇— |
| n-C₄H₉— | C₂H₅— | ZnCl₂ | (CH₃CO)₂O | n-C₄H₉— |
| n-C₄H₉— | C₂H₅— | AlCl₃ | (CH₃CO)₂O | n-C₄H₉— |
| n-C₄H₉— | i-C₃H₇— | ZnCl₂ | (CH₃CO)₂O | n-C₄H₉— |
| s-C₄H₉— | CH₃— | ZnCl₂ | (CH₃CH₂CO)₂O | s-C₄H₉— |
| s-C₄H₉— | t-C₄H₉— | AlCl₃ | (CH₃CO)₂O | s-C₄H₉— |
| s-C₄H₉— | n-C₄H₉— | AlCl₃ | (CH₃CO)₂O | s-C₄H₉— |
| s-C₄H₉— | s-C₄H₉— | BF₃ | (CH₃CH₂CH₂CO)₂O | s-C₄H₉— |
| t-C₄H₉— | CH₃— | ZnCl₂ | (CH₃CO)₂O | t-C₄H₉— |
| t-C₄H₉— | n-C₃H₇— | ZnCl₂ | (CH₃CO)₂O | t-C₄H₉— |
| t-C₄H₉— | i-C₃H₇— | BF₃ | (CH₃CHCO)₂O \| CH₃ | t-C₄H₉— |

EXAMPLE 31

The pre-emergence and post-emergence herbicidal activity of typical representatives of the compounds of the present invention are set forth below, together with the test procedures.

TEST PROCEDURES

Pre-emergence

Appropriate weed species are seeded in individual disposable four-inch square containers and watered only in amounts adequate to moisten soil. The samples are stored for twenty-four hours before treatment.

Post-emergence

The weed species are seeded by growth-time requirement schedules in individual disposable four-inch square containers, watered as required, and maintained under greenhouse conditions. When all the weeds have reached suitable growth development, generally first true leaf stage, those appropriate to pertaining test requirements are selected for uniformity of growth and development. One four-inch container of each weed, averaging up to fifty (Crabgrass) or more weeds per individual container, is then placed on a carrying tray for treatment. Generally eight weed containers are used in each evaluation.

Formulation and Treatment

The candidate compounds are dissolved in acetone or other suitable solvent and, as appropriate, diluted in water containing wetting and emulsifying agents.

One carrying tray each of pre-emergence and post-emergence containers, mounted on a conveyer belt of 1.5 m.p.h. linear speed, trips a microswitch which in turn activates a solenoid valve and releases treatment. Candidate compounds are discharged as sprays at a rate of forty gallons (adjustable) per acre and thirty pounds (adjustable) pressure. Pre-emergence and post-emergence treatments are removed to the greenhouse and held for observation.

2,4-D (2,4-dichlorophenoxyacetic acid) is used as a reference standard.

Observations

Post-emergence treatments are observed daily for interim response, final observations being made fourteen days after treatment, while pre-emergence observations are made up to 21 days after treatment. Any treatments inducing questionable response are held beyond the 14-day or 21-day observation period until such responses can be confirmed.

Observations include all abnormal physiological responses of stem bending, petiole curvature, epinasty, hyponasty, retardation, stimulation, root development, necrosis and related growth regulant characteristics.

The results are listed in the following tables. The compounds of the present invention are particularly effective against deep or shallow germinating broadleaf annual weeds such as Wild Morning Glory (MNG). This latter weed is especially troublesome in the cultivation of the soybean plant.

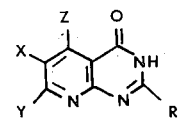

| Y | X | Z | R | Lbs./Acre | BNG | MNG | MST | JMW |
|---|---|---|---|---|---|---|---|---|
| H | Cl | H | —$CF_3$ | 2 | 9:Ne | 10:RNe | 10:RNe | 10:RNe |
|   |   |   |   | 1 | 9:Ne | 9:RNe | 10:RNe | 10:RNe |
|   |   |   |   | .5 | 8:Ne | 5:R | 10:RNe | 5:RNe |
| H | Cl | H | —$CF_2CF_3$ | 2 | 7:RNe | 9:RNe | 10:RNe | 9:RNe |
|   |   |   |   | 1 | 5:R | 8:RNe | 9:RNe | 5:RNe |
|   |   |   |   | .5 | 3:R | 7:RNe | 8:RNe | 4:RNe |
| H | H | H | —$CF_2CF_3$ | 5 | 0:O | 8:Ne | 9:RNe | 0:O |
| H | Br | H | —$CF_2CF_3$ | 2 | 0:O | 6:RNe | 9:Ne | 0:O |
|   |   |   |   | 1 | 0:O | 4:RNe | 8:RNe | 0:O |
|   |   |   |   | .5 | 0:O | 0:O | 3:Ne | 0:O |
| H | Br | H | —$CF_3$ | 2 | 8:Ne | 9:Ne | 9:RNe | 10:Ne |
|   |   |   |   | 1 | 5:R | 5:RNe | 9:RNe | 10:Ne |
|   |   |   |   | .5 | 4:R | 3:Ne | 9:RNe | 8:Ne |
| H | H | H | —$CF_2Cl$ | 5 | 0:O | 2:RCl | 4:RNe | 0:O |
| H | H | H | —$CF_2CFClH$ | 5 | 0:O | 0:O | 3:RNe | 0:O |
| H | Cl | H | —$CF_2Cl$ | 5 | 1:Ne | 10:Ne | 10:Ne | 10:RNe |
|   |   |   |   | 2 | 0:O | 3:R | 6:R | 3:RNe |
|   |   |   |   | 1 | 0:O | 0:O | 2:R | 2:R |
| H | Cl | H | —$CF_2CFClH$ | 5 | 3:RNe | 10:Ne | 10:RNe | 10:RNe |
|   |   |   |   | 2 | 0:O | 5:RCl | 10:RNe | 7:Ne |
|   |   |   |   | 1 | 0:O | 5:RCl | 9:RNe | 3:Ne |
| H | Cl | H | —$CF_2CF_2H$ | 5 | 10:Ne | 10:Ne | 10:RNe | 10:RNe |
|   |   |   |   | 2 | 0:O | 8:RNe | 10:Ne | 10:RNe |
|   |   |   |   | 1 | 0:O | 7:R | 10:Ne | 5:RNe |
|   |   |   |   | .5 | 0:O | 0:O | 5:Ne | 2RNe |
| H | Br | H | —$CF_2Cl$ | 5 | 0:O | 4:RNe | 8:RNe | 0:O |
| H | Br | H | —$CF_2CFClH$ | 5 | 7:Ne | 9:R | 10:RNe | 10:Ne |
|   |   |   |   | 2 | 0:O | 9:RNe | 8:R | 2:RNe |
|   |   |   |   | 1 | 0:O | 8:RNe | 5:R | 0:O |
| H | Br | H | —$CF_2CF_2H$ | 5 | 8:Ne | 9:R | 10:Ne | 10:Ne |
|   |   |   |   | 2 | 3:R | 10:RNe | 9:RNe | 8:RNe |
|   |   |   |   | 1 | 2:R | 9:RNe | 7:R | 5:RNe |
|   |   |   |   | .5 | 0:O | 5:R | 7:R | 4:R |
| $CH_3$ | $CH_3$ | H | —$CF_2CFClH$ | 5 | 0:O | 0:O | 2:R | 0:O |
| $CH_3$ | Cl | $CH_3$ | —$CF_3$ | 10 | 2:R | 0:O | 8:R | 5:RNe |
| $CH_3$ | H | $CH_3$ | —$CF_3$ | 5 | 7:Ne | 10:Ne | 10:Ne | 10:Ne |

-continued

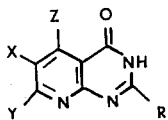

| Y | X | Z | R | Lbs./Acre | Herbicide Pre-Emergence Tests Plant* | | | |
|---|---|---|---|---|---|---|---|---|
| | | | | | BNG | MNG | MST | JMW |
| | | | | 2 | 0:O | 2:Ne | 9:RNe | 8:RNe |
| | | | | 1 | 0:O | 0:O | 5:R | 6:RNe |
| H | Cl | H | —C(CH₃)₃ | 2 | 6:RNe | 9:Ne | 9:Ne | 5:RCl |
| | | | | 1 | 4:RNe | 10:Ne | 8:Ne | 7:RNe |
| | | | | .5 | 3:Ne | 9:Ne | 8:Ne | 4:RNe |
| H | H | H | —C(CH₃)₃ | 5 | 5:RNe | 10:Ne | 10:Ne | 10:Ne |
| | | | | 2 | 1:Ne | 5:RNe | 7:RNe | 4:RCl |
| H | Cl | H | —CH₂CH(CH₃)₂ | 5 | 8:RNe | 9:Ne | 10:RNe | 10:RNe |
| | | | | 2 | 0:O | 0:O | 0:O | 0:O |
| H | Cl | H | —CH(CH₃)₂ | 4 | 9:RNe | 9:Ne | 10:Ne | 10:Ne |
| | | | | 2 | 5:RNe | 6:Ne | 10:Ne | 10:Ne |
| | | | | 1 | 2:R | 2:Cl | 9:RNe | 5:RNe |
| H | Cl | H | —(CH₂)₃CH₃ | 5 | 7:R | 2:Ne | 5:R | 5:RNe |
| | | | | 2 | 2:R | 0:O | 7:RNe | 0:O |
| | | | | 1 | 1:R | 0:O | 0:O | 0:O |
| H | Cl | H | —CH(CH₃)C₂H₅ | 5 | 7:RNe | 9:Ne | 10:RNe | 10:RNe |
| | | | | 1 | 2:R | 2:Cl | 5:R | 3:RNe |

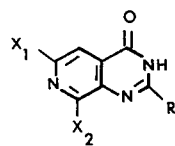

| X₁ | X₂ | R | Lbs./Acre | BNG | MNG | Plant* MST | JMW |
|---|---|---|---|---|---|---|---|
| H | H | —CF₃ | 10 | 5:R | 8:R | 9:R | 9:R |
| Cl | Cl | —CF₃ | 10 | 1:Ne | 2:RCl | 9:RNe | 8:RNe |
| Br | Br | —CF₃ | 10 | 1:Ne | 2:RHy | 2:RCl | 0:O |

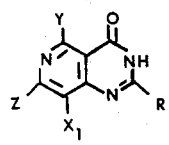

| Y | X₁ | Z | R | Lbs./Acre | BNG | MNG | MST | JMW |
|---|---|---|---|---|---|---|---|---|
| H | Cl | H | —CF₃ | 10 | 3:RNe | 9:R | 10:R | 10:RNe |
| | | | | 8 | 3:Ne | 8:R | 7:RNe | 8:R |
| | | | | 2 | 2:Ne | 5:R | 5:R | 0:O |

*Plants (Annual Weeds) — Plant Injury and Response

BNG - Barnyard grass — R - Retarded or reduced
MST - Mustard — Ne - Necrosis
MNG - Wild morning glory — D - Distorted
JMW - Jimsonweed — C - Caustic
Ro - Root
Herbicidal Numerical Injury — P - Phytotoxicity
Rating — Ep - Epinasty
0 (no injury) to — A - Albinism
10 (all plants killed). — Cl - Chlorosis

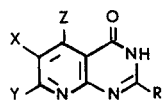

| | | | | Lbs./ | Herbicide Post-Emergence Tests Plant* | | | |
|---|---|---|---|---|---|---|---|---|
| Y | X | Z | R | Acre | BNG | MNG | MST | JMW |
| H | Cl | H | —CF₃ | 1 | 10:Ne | 10:Ne | 10:Ne | 10:Ne |
| | | | | .25 | 10:Ne | 10:Ne | 10:Ne | 9:Ne |
| H | Cl | H | —CF₂CF₃ | 1 | 10:Ne | 10:Ne | 10:Ne | 10:Ne |
| | | | | .25 | 10:Ne | 7:Ne | 10:Ne | 9:Ne |
| H | H | H | —CF₂CF₃ | 2 | 0:O | 1:Ne | 10:Ne | 5:Ne |
| | | | | 1 | 0:O | 1:Ne | 10:Ne | 6:RNe |
| | | | | .5 | 0:O | 0:O | 9:Ne | 4:RNe |
| H | Br | H | —CF₂CF₃ | 2 | 10:Ne | 10:Ne | 10:Ne | 10:Ne |
| | | | | 1 | 10:Ne | 10:Ne | 10:Ne | 10:Ne |
| | | | | .5 | 7:Ne | 7:Ne | 10:Ne | 10:Ne |
| H | Br | H | —CF₃ | 2 | 10:Ne | 9:Ne | 10:Ne | 10:Ne |
| | | | | 1 | 10:Ne | 8:Ne | 10:Ne | 10:Ne |
| | | | | .5 | 10:Ne | 9:Ne | 10:Ne | 10:Ne |
| H | H | H | —CF₂Cl | 2 | 2:R | 5:RNe | 10:Ne | 10:Ne |
| H | H | H | —CF₂CHFCl | 2 | 0:O | 5:RNe | 10:Ne | 8:RNe |
| H | Cl | H | —CF₂Cl | 2 | 9:Ne | 10:Ne | 10:Ne | 10:Ne |
| | | | | 1 | 8:Ne | 10:Ne | 10:Ne | 10:Ne |
| | | | | .5 | 7:Ne | 4:Ne | 10:Ne | 10:Ne |
| H | Cl | H | —CF₂CHFCl | 1 | 10:Ne | 10:Ne | 10:Ne | 10:Ne |
| | | | | .5 | 10:Ne | 10:Ne | 10:Ne | 10:Ne |
| | | | | .25 | 10:Ne | 10:Ne | 10:Ne | 10:Ne |
| H | Cl | H | —CF₂CF₂H | 1 | 10:Ne | 10:Ne | 10:Ne | 10:Ne |
| | | | | .5 | 10:Ne | 10:Ne | 10:Ne | 10:Ne |
| H | Br | H | —CF₂Cl | 1 | 4:RNe | 5:Ne | 10:Ne | 10:Ne |
| | | | | .25 | 2:RNe | 3:Ne | 8:Ne | 8:Ne |
| H | Br | H | —CF₂CHFCl | 2 | 10:Ne | 10:Ne | 10:Ne | 10:Ne |
| | | | | 1 | 9:Ne | 10:Ne | 10:Ne | 10:Ne |
| H | Br | H | —CF₂CF₂H | 1 | 10:Ne | 10:Ne | 10:Ne | 10:Ne |
| | | | | .25 | 10:Ne | 8:Ne | 10:Ne | 10:Ne |
| CH₃ | CH₃ | H | —CF₂CHFCl | 2 | 3:RNe | 7:RNe | 10:Ne | 10:Ne |
| | | | | .5 | 0:O | 0:O | 5:RNe | 9:RNe |
| CH₃ | Cl | CH₃ | —CF₃ | 5 | 2:Ne | 0:O | 10:Ne | 10:Ne |
| CH₃ | H | CH₃ | —CF₃ | 2 | 5:RNe | 10:Ne | 10:Ne | 10:Ne |
| | | | | .5 | 2:RNe | 2:RNe | 10:Ne | 0:O |
| | | | | .25 | 2:R | 1:Ne | 9:Ne | 0:O |
| CH₃ | Cl | H | —CF₂CHFCl | 2 | 2:Ne | 2:Ne | 2:Ne | 9:Ne |
| | | | | 1 | 1:Ne | 2:RNe | 9:Ne | 0:O |
| | | | | .5 | 1:Ne | 1:Ne | 9:Ne | 0:O |
| H | Cl | H | —C(CH₃)₃ | 1 | 5:NeCl | 10:Ne | 10:Ne | 10:Ne |
| | | | | .5 | 4:NeCl | 8:Ne | 10:Ne | 10:Ne |
| | | | | .25 | 2:Ne | 7:Ne | 9:Ne | 9:Ne |
| H | H | H | —C(CH₃)₃ | 1 | 4:RNe | 4:RCl | 4:RNe | 3:RCl |
| | | | | .5 | 1:Ne | 2:Cl | 2:Ne | 2:RCl |
| | | | | .25 | 1:Ne | 1:Cl | 1:Cl | 1:Cl |
| H | Cl | H | —CH₂CH(CH₃)₂ | 2 | 2:NeCL | 3:Ne | 2:Ne | 3:NeCl |
| H | Cl | H | —CH(CH₃)₂ | 2 | 4:RNe | 4:Ne | 10:Ne | 10:Ne |
| | | | | .5 | 0:O | 9:Ne | 7:Ne | 10:Ne |
| H | Cl | H | —(CH₂)₃CH₃ | 1 | 0:O | 4:RNe | 10:Ne | 9:Ne |
| | | | | .5 | 0:O | 2:R | 2:RNe | 7:Ne |
| H | Cl | H | —CH(CH₃)C₂H₅ | 1 | 2:R | 1:R | 5:R | 10:Ne |
| | | | | .5 | 1:R | 1:R | 5:R | 9:Ne |

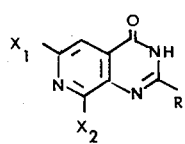

| X₁ | X₂ | R | Lbs./Acre | BNG | MNG | MST | JMW |
|---|---|---|---|---|---|---|---|
| Cl | Cl | —CF₃ | 5 | 1:Ne | 4:RNe | 10:Ne | 10:Ne |
| Br | Br | —CF₃ | 5 | 1:Cl | 1:NeCl | 10:Ne | 9:Ne |
| H | H | —CF₃ | 5 | 10:Ne | 10:Ne | 10:Ne | 10:Ne |

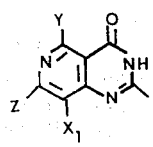

| Y | $X_1$ | Z | R | Lbs./Acre | BNG | MNG | Plant* MST | JMW |
|---|---|---|---|---|---|---|---|---|
| H | Cl | H | $CF_3$ | 5 | 3:Ne | 3:RNe | 10:Ne | 10:Ne |

*Plants (Annual Weeds)    Plant Injury and Response

| | |
|---|---|
| BNG - Barnyard grass | R - Retarded or reduced |
| MST - Mustard | Ne - Necrosis |
| MNG - Wild morning glory | D - Distorted |
| JMW - Jimsonweed | C - Caustic |
| | Ro - Root |
| Herbicidal Numerical Injury Rating | P - Phytotoxicity |
| 0 (no injury) to | Ep - Epinasty |
| 10 (all plants killed). | A - Albinism |
| | Cl - Chlorosis |

Preparation A

Halogenated Acids a. 2,2-Difluoro-3-chloropropionic Acid 2,2-Difluoropropionic acid, prepared by the method of Henne, et al., *J. Am. Chem. Soc.*, 69, 281 (1947), is chlorinated by the procedure of England, et al., *J. Am. Chem. Soc.*, 80, 6442 (1958), wherein chlorine gas is bubbled through a sintered glass dispersion tube into the starting acid in a quartz flask fitted with a well containing a GE H85-C3 mercury vapor lamp. After radiation overnight the product is distilled under reduced pressure.

Employing the procedures indicated in the noted references, the following, noncommercial halogenated acids are prepared as intermediates leading to the products of the instant invention.

| | | | |
|---|---|---|---|
| | | | $LMNC\text{-}CF_2CO_2H$ |
| L | M | N | Reference |
| H | H | H | a |
| H | F | F | b |
| H | Cl | Cl | b |
| Cl | Cl | Cl | b |
| H | F | Cl | b |
| F | Cl | Cl | b |

"Henne, et al., J. Am. Chem. Soc., 69, 281 (1947)
"England, et al., J. Am. Chem. Soc., 80, 6442 (1958)

Preparation B

Halogenated Acid Anhydrides and Acid Chlorides a. Fluoroalkanoic Acid Anhydrides The following fluoroalkanoic acid anhydrides, not commercially available, are synthesized from the corresponding fluoroalkanoic acid and phosphorous pentoxide according to the method as taught by England, et al., *J. Am. Chem. Soc.*, 80, 6442 (1958), which comprises a slow distillation of the anhydride from a mixture of the corresponding acid and phosphorous pentoxide:

| | $(R_1CF_2CO)_2O$ |
|---|---|
| $R_1$ | $R_1$ |
| H— | $ClF_2C$— |
| Cl— | $F_2HC$— |
| $F_3C$— | $FClHC$— |
| $CH_3$ | $FCl_2C$— | b. Fluoroalkanoic Acid Chlorides

The following acid chlorides are prepared from the acid and benzotrichloride, essentially the method employed by England, et al.:

| | $R_1CF_2COCl$ |
|---|---|
| $R_1$ | $R_1$ |
| $F_3C$— | $Cl_2HC$— |
| $CH_3$— | $Cl_3C$— |
| $F_2HC$— | $ClF_2C$— |
| Cl— | $FClHC$— |
| H— | $FCl_2C$— |

Preparation C

Alkanoic and Cycloalkanoic Acid Anhydrides and Acid Chlorides a. The alkanoic and cycloalkanoic acid anhydrides employed as starting reagents leading to the synthesis of subject compounds are either commercial chemicals or are easily prepared according to literature procedures, such as those summarized by Wagner & Zook, "Snythetic Organic Chemistry," John Wiley & Sons, Inc., New York, New York, 1953, Chapter 18, page 558.

b. Similarly, the alkanoic and cycloalkanoic acid chlorides are commercially available or reported in the chemical literature as being synthesized by methods known to those skilled in the art and summarized by Wagner & Zook, "Synthetic Organic Chemistry," John Wiley & Sons, Inc., New York, New York, 1953, Chapter 17, page 546.

Preparation D

2-Aminonicotinic Acid and Its Derivatives a. 2Aminonicotinic acid is a commercially available reagent or can be easily prepared according to the method as taught by Taylor, et al., *J. Org. Chem.*, 19, 1633 (1954).

b. 2-Amino-5-alkylnicotine acids

The following 2-aminonicotinic acids are synthesized from the corresponding 2-aminonicotinonitriles of Example 30 via acid hydrolysis employing the procedure of Taylor, et al., *J. Org. Chem.*, 19, 1633 (1954):

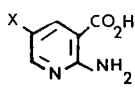

| X | X |
|---|---|
| $CH_3$ | $t-C_4H_9$ |
| $C_2H_5$ | $s-C_4H_9$ |
| $n-C_3H_7$ | $n-C_4H_9$ |
| $i-C_3H_7$ | | c. 2-Amino-4,6-dimethylnicotinamide is synthesized according to the method of Dornow, et al., *Chem. Ber.*, 84, 296 (1951).

d. 2-Amino-4,6-dimethylnicotinic acid hydrochloride is prepared by a modification of the procedure of Dornow, et al., *Chem. Ber.*, 73, 542 (1940) wherein the free acid is not liberated by the addition of aqueous sodium hydroxide solution but is isolated as the hydrochloride salt by evaporation of the reaction mixture.

e. 2-Amino-4,5,6-trimethylnicotinic acid is prepared according to the procedure of Dornow, et al., *Arch. Pharm.*, 290, 20 (1951).

f. Employing the experimental procedure of Dornow, et al., *Chem. Ber.*, 84, 296 (1951), 2-amino-5,6-dimethylnicotinamide is synthesized.

g. 2Amino-5-chloronicotinic acid and hydrochloride

A suspension of 40.0 g. of 2-aminonicotinic acid in 2 l. of acetic acid is stirred while chlorine gas is bubbled through the reaction mixture at a moderate rate for 1.25 hrs. The resulting solution is allowed to stir at ambient temperatures for 20 hrs., and is then treated with an equal volume of diethyl ether. The resulting precipitate of 2-amino-5-chloronicotinic acid hydrochloride is filtered, washed with ether and dried in vacuo at 80° C. for several hours, 51.0 g., m.p. 251° C. (dec.).

The free acid is obtained by treating a cold aqueous solution of the hydrochloride salt with sufficient ammonium hydroxide to provide a pH 5. The resulting product is filtered, washed with a small amount of acetone and dried in vacuo.

h. 2-Amino-5-bromonicotinic acid and hydrobromide

In a manner similar to Preparation D-g, 3.6 g. of 2-aminonicotinic acid in 450 ml. of acetic acid is treated dropwise over a period of 10-15 min. with 4 ml. of bromine in 50 ml. of the same solvent. The reaction mixture is allowed to stir at room temperature for 1.5–2 hrs., and is then diluted with 2 l. of diethyl ether. The precipitate which is formed, 2-amino-5-bromonicotinic acid hydrobromide, is filtered and dried, 5.6 g., m.p. 280° C. (dec.).

The free acid is liberated by adding sufficient ammonium hydroxide to an aqueous solution of the hydrobromide salt to provide a solution of pH 5. The resulting free acid is filtered from the cooled mixture and dried in vacuo.

i. 2-Amino-5-chloro-6-methylnicotinic acid hydrochloride

In a manner similar to that of Preparation D-g, 2-amino-6-methylnicotinic acid, synthesized by the method of Dornow, et al., *Chem. Ber.*, 73, 542 (1940), is chlorinated in acetic acid to provide the desired product.

j. 2-Amino-4-methyl-5-chloronicotinic acid hydrochloride

3-Cyano-4-methylpyridine, Webb, et al., *J. Am. Chem. Soc.*, 66, 1456 (1944), is converted via the sequences of Taylor, et al., *J. Org. Chem.*, 19, 1633 (1954) to 2-amino-4-methylnicotinic acid, which under the conditions of Preparation D-g is chlorinated at the 5-position to provide the desired intermediate, 2-amino-4-methyl-5-chloronicotinic acid hydrochloride.

k. 2-Amino-4-methyl-5-bromonicotinic acid hydrobromide.

In a manner analogous to that of Preparation D-h, 2-amino-4-methylnicotinic acid is brominated in an acetic acid solvent to provide the desired compounds in good yields.

l. 2-Amino-5-chloro-6- and 4-methylnicotinamide

Fifty grams of 2amino-5-chloronicotinic acid hydrochloride is added in small portions to 185 ml. of cold (3° C.) acetyl chloride containing 80 g. of phosphorous pentachloride and the resulting reaction mixture allowed to stir at room temperature for 16 hrs. The precipitate which has formed is filtered, washed with 150 ml. of methylene chloride and partially dissolved in 1.2 l. of acetonitrile. While the solution of 2-amino-5-chloronicotinic acid chloride is being stirred at ambient temperatures, ammonia gas is bubbled through the slurry for 40 min. at a moderate rate. The solids are filtered and the residue, remaining after the filtrate is concentrated to dryness, is partially dissolved in acetone. The acetone suspension is filtered and the filtrate concentrated in vacuo to give 13.9 g. of the desired nicotinamide, m.p. 227°–229° C.

Similarly, by starting with 2-amino-5-chloro-4-metylnicotinic acid hydrochloride and repeating the above procedure, the corresponding 2-amino-5-chloro-4-methylnicotinamide is prepared.

m. 2-Amino-5-bromo-4- and 6-methylnicotininamide

Starting with 2-amino-5-bromo-4-methylnicotinic acid hydrobromide and 2-amino-5-bromo-6-methylnicotinic acid hydrobromide and repeating the procedure of Preparation D-1, the corresponding nicotinamides are prepared.

n. 2-Amino-4,6-dimethyl-5-chloronicotinic acid hydrochloride

Chlorine gas is bubbled through a solution of 1.89 g. of 2-amino-4,6-dimethylnicotinic acid hydrochloride in 150 ml. of acetic acid at 36° C. for 20-25 min. The resulting solid is filtered, washed with diethyl ether and dried, 1.29 g., m.p. 232°–234° C. (dec.).

o. 2-Amino-4,6-dimethyl-5-bromonicotinic acid is prepared by the procedure of Dornow, et al., *Arch. Pharm.*, 290, 20 (1951).

p. 2-Amino-5-alkylnicotinonitriles 1. 2-amino-4-methyl-5-ethylnicotinonitrile

To 67.0 g. (0.5 mole) of 1-methylbutylidene malononitrile (Cope, et al., *J. Am. Chem. Soc.*, 63 733 (1941) is added 260 ml. of acetic anhydride and 50 ml. of triethyl orthoformate and the resulting solution heated to reflux for 18 hrs. The reaction mixture is concentrated under reduced pressure, and the residue is dissolved in 300 ml. of acetonitrile. Ammonia gas is bubbled through the reaction mixture at a moderate rate for 2 hrs., and the mixture then heated to reflux for 4 hrs. The solvent is removed from the filtered mixture under reduced pressure and the residual material triturated with diethyl ether. Filtration and drying gave the desired crude product.

The above reaction procedure is repeated, employing the indicated malononitrile and ortho ester starting materials to provide the corresponding substituted 2-aminonicotinonitriles:

nium hydroxide to provide a pH 5. The free acid is then filtered and dried.

Preparation F

3-Aminoisonicotinic Acid and Its Derivatives a. 3-Amino-2,6-dibromoisonicotinic acid A slurry of 1.38 g. of 3-aminoisonicotinic acid in 25 ml. of acetic acid and cooled to 15° C. in an ice-water bath is treated dropwise with 3.2 g. of bromine in 6 ml. of the same solvent. When the addition is complete, the reaction mixture is allowed to stir at 10°–15° C. for an additional 30 min. and at room temperature for 45 min. Diethyl ether (300 ml.) is added to the reaction mixture and the resulting precipitate is filtered and dried, m.p. 251°–253°C.

The free acid is liberated from the hydrobromide in the usual manner employing ammonium hydroxide.

b. In a manner similar to Preparation F-a, 5.0 g. of

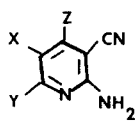

| Starting Materials | | | Product | |
|---|---|---|---|---|
| Malononitrile | ortho ester | Y | X | Z |
| $CH_3CH_2CH_2C(CH_3)=C(CN)_2$ | $CH_3C(OC_2H_5)_3$ | $CH_3-$ | $C_2H_5-$ | $CH_3-$ |
| $CH_3(CH_2)_3CH=C(CN)_2$ | $CH_3C(OC_2H_5)_3$ | $CH_3-$ | $n-C_3H_7-$ | $H-$ |
| $CH_3(CH_2)_3C(CH_3)=C(CN)_2$ | $CH_3C(OC_2H_5)_3$ | $CH_3-$ | $n-C_3H_7-$ | $CH_3-$ |
| $(CH_3)_2CHCH_2C(CH_3)=C(CN)_2$ | $CH_3C(OC_2H_5)_3$ | $CH_3-$ | $i-C_3H_7-$ | $CH_3-$ |
| $CH_3(CH_2)_4CH=C(CN)_2$ | $CH_3C(OC_2H_5)_3$ | $CH_3-$ | $n-C_4H_9-$ | $H-$ |
| $CH_3(CH_2)_4C(CH_3)=C(CN)_2$ | $CH_3C(OC_2H_5)_3$ | $CH_3-$ | $n-C_4H_9-$ | $CH_3-$ |
| $CH_3CH(C_2H_5)CH_2C(CH_3)=C(CN)_2$ | $HC(OC_2H_5)_3$ | $H-$ | $s-C_4H_9-$ | $CH_3-$ |
| $(CH_3)_3CCH_2C(CH_3)=C(CN)_2$ | $CH_3C(OC_2H_5)_3$ | $CH_3-$ | $t-C_4H_9-$ | $CH_3-$ |

Preparation E

4-Aminonicotinic Acid and Its Derivatives a. 4-Aminonicotinic acid is conveniently synthesized by the method of Fox, *J. Org. Chem.*, 17, 547 (1952) or Bachman, et al., *J. Org. Chem.*, 14, 97 (1949).

b. 4-Amino-5-bromonicotinic acid

A solution of 13.8 g. of 4-aminonicotinic acid in 250 ml. of acetic acid is treated dropwise with 31 g. of bromine in 75 ml. of the same solvent. After the addition is complete, the reaction is allowed to stir for an additional 2 hrs. and is then diluted with diethyl ether. The precipitated product is partially suspended in water and sufficient ammonium hydroxide added to provide a pH 5. The mixture is subsequently cooled in an ice bath and filtered. The cake is washed with ether and dried in vacuo.

In a similar manner, starting with 4-amino-6-methylnicotinic acid, the corresponding 4-amino-5-bromo-6-methylnicotinic acid is prepared.

c. 4-Amino-2,6-dimethylnicotinic acid is synthesized according to the procedure of Wang, et al., *Tetrahedron*, 27, 2581 (1971).

d. 4-Amino-5-chloronicotinic acid.

Chlorine gas is slowly bubbled into a solution of 20.7 g. of 4-aminonicotinic acid in 225 ml. of acetic acid. After 45 min. the gas inlet is removed and the mixture allowed to stir overnight. Diethyl ether (1.5 l.) is added and the solid precipitate filtered. A suspension of the product in water is treated with sufficient ammo- 3-aminoisonicotinic acid is chlorinated with 5.2 g. of chlorine in 250 ml. of acetic acid at a reaction temperature of 15°–20° C. Dilution of the reaction mixture with 700 ml. of diethyl ether gave a precipitate which proved to be starting material; the filtrate, on concentration to dryness, contains the desired product which is slurried several times in ether, 2.0 g., m.p. 235°–239° C.

The free acid is generated from the hydrochloride salt by treatment of an aqueous solution of the salt with ammonium hydroxide to pH 5 in the aforementioned manner.

c. 2- and 6-Chloro-3-aminoisonicotinic acid

A solution of 1.38 g. of 3-aminoisonicotinic acid in 15 ml. of methanol cooled to −45° C. in an acetone-dry ice bath is treated with 800 mg. of chlorine which is bubbled through the reaction mixture at a slow rate. The reaction mixture is allowed to stir in the cold until thin layer chromatography indicates the starting material has completely reacted. The mixture is poured into 50 ml. of water and ammonium hydroxide added until a pH of 5 is achieved. The crude product is subjected to thick layer perparative chromatography in order to separate the two mono chlorinated products, the 6-isomer being the predominant product. The material containing the separated isomers is scraped from the thick plate and the products eluted with acetonitrile. Removal of the solvent invacuo provides the two mono chlorinated intermediates.

d. 2- and 6-Bromo-3-aminoisonicotinic acid

The procedure of Preparation F-c is repeated, employing 3-aminoisonicotinic acid and one equivalent of bromine, to provide a mixture of the two mono bromo isomers in which the 6-bromo isomer is dominant. The two isomers are conveniently separated employing preparative thick layer chromatography.

Preparation G 1,1,3,3-Tetraalkoxypropanes a. The 1,1,3,3-tetraalkoxypropanes employed in the synthesis of 2-aminonicotinonitrile are either commercial reagents or can readily be synthesized by methods known to those skilled in the art, for example, those of Protopapova, et al., Zhur. Obshchei. Khim., 27, 57 (1957)(C.A., 51, 11990a), U.S. Pat. 2,823,226, U.S. Pat. No. 2,786,081 or Japan Pat. 5327 (C.A., 51, 15557).

What is claimed is:

1. The process for preparing 2-aminonicotinonitrile, which process comprises:
    1. reacting equimolar proportions of a 1,1,3,3-tetraalkoxypropane wherein said alkoxy group contains from 1 to 4 carbon atoms with malononitrile in the presence of at least three molar equivalents of an alkanoic acid anhydride wherein said alkanonic acid contains from 2 to 4 carbon atoms at 30°–200°C. and
    2. thereafter, reacting the intermediate 1-alkoxy-4,4-dicyano-1,3-butadiene product with equimolar proportions of ammonia at 25°–100°C. in a reaction inert solvent.

2. The process for preparing 2-aminonicotinonitrile as claimed in claim 1 wherein a 1,1,3,3-tetraalkoxypropane is reacted with malononitrile in the presence of a catalytic amount of chloride.

3. The process for preparing 2-aminonicotinonitrile as claimed in claim 2 wherein the 1,1,3,3-tetraalkoxypropane is 1,1,3,3-tetramethoxypropane and the alkanoic acid anhydride is acetic anhydride.

* * * * *